US 10,314,844 B2
Jun. 11, 2019

(12) United States Patent
Lee et al.

(10) Patent No.: US 10,314,844 B2
(45) Date of Patent: Jun. 11, 2019

(54) INHIBITORS OF BRUTON'S TYROSINE KINASE

(71) Applicants: GILEAD SCIENCES, INC., Foster City, CA (US); ONO PHARMACEUTICAL CO., LTD., Osaka (JP)

(72) Inventors: Seung H. Lee, Sammamish, WA (US); Shingo Yamamoto, Osaka (JP)

(73) Assignees: GILEAD SCIENCES, INC., Foster City, CA (US); ONO PHARMACEUTICAL CO., LTD., Osaka (JP)

(*) Notice: Subject to any disclaimer, the term of this patent is extended or adjusted under 35 U.S.C. 154(b) by 0 days.

(21) Appl. No.: 15/903,295

(22) Filed: Feb. 23, 2018

(65) Prior Publication Data

US 2018/0243311 A1 Aug. 30, 2018

Related U.S. Application Data

(60) Provisional application No. 62/463,176, filed on Feb. 24, 2017.

(51) Int. Cl.
| | | |
|---|---|---|
| *A61K 31/522* | (2006.01) | |
| *A61P 35/02* | (2006.01) | |
| *A61P 29/00* | (2006.01) | |
| *A61P 37/08* | (2006.01) | |
| *A61P 25/28* | (2006.01) | |
| *A61P 13/12* | (2006.01) | |
| *A61P 3/04* | (2006.01) | |
| *A61P 31/12* | (2006.01) | |
| *A61P 9/00* | (2006.01) | |
| *C07D 473/34* | (2006.01) | |

(52) U.S. Cl.
CPC .............. *A61K 31/522* (2013.01); *A61P 3/04* (2018.01); *A61P 9/00* (2018.01); *A61P 13/12* (2018.01); *A61P 25/28* (2018.01); *A61P 29/00* (2018.01); *A61P 31/12* (2018.01); *A61P 35/02* (2018.01); *A61P 37/08* (2018.01); *C07D 473/34* (2013.01); *A61K 2121/00* (2013.01)

(58) Field of Classification Search
CPC ..... A61K 31/522; A61K 2121/00; A61P 9/00; A61P 31/12; A61P 3/04; A61P 13/12; A61P 37/08; A61P 29/00; A61P 35/02; A61P 25/28; C07D 473/34
See application file for complete search history.

(56) References Cited

U.S. PATENT DOCUMENTS

| 4,943,593 A | 7/1990 | Palfreyman et al. |
|---|---|---|
| 4,965,288 A | 10/1990 | Palfreyman et al. |
| 4,997,854 A | 3/1991 | Kagan et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,252,608 A | 10/1993 | Palfreyman et al. |
| 7,514,444 B2 | 4/2009 | Honigberg et al. |
| 8,450,321 B2 | 5/2013 | Mitchell et al. |
| 8,501,724 B1 | 8/2013 | Chen et al. |
| 8,557,803 B2* | 10/2013 | Yamamoto ........... C07D 473/34 514/210.18 |
| 8,940,725 B2* | 1/2015 | Yamamoto ........... C07D 473/34 514/210.18 |
| 8,940,893 B2 | 1/2015 | Bosanac et al. |
| 9,199,997 B2* | 12/2015 | Yamamoto ........... A61K 31/522 |
| 9,371,325 B2 | 6/2016 | Yamamoto et al. |
| 9,550,835 B2 | 1/2017 | Ono et al. |
| 9,896,453 B2* | 2/2018 | Yamamoto ........... A61K 31/522 |
| 9,926,322 B2* | 3/2018 | Yamamoto ........... C07D 473/34 |
| 2004/0248871 A1 | 12/2004 | Farjanel et al. |
| 2009/0142345 A1 | 6/2009 | Satou et al. |
| 2010/0120717 A1* | 5/2010 | Brown .................. C07D 241/18 514/81 |
| 2011/0287011 A1 | 11/2011 | Gurney et al. |
| 2014/0142099 A1 | 5/2014 | Owens |
| 2015/0175616 A1 | 6/2015 | Blomgren et al. |

FOREIGN PATENT DOCUMENTS

| EP | 2786996 A1 | 10/2014 |
|---|---|---|
| WO | 2005113556 A1 | 12/2005 |
| WO | 2008121742 A2 | 10/2008 |
| WO | 2009035791 A1 | 3/2009 |
| WO | 2011008709 A1 | 1/2011 |
| WO | 2009017833 A1 | 2/2011 |
| WO | 2011097513 A1 | 8/2011 |
| WO | 2012027721 A1 | 3/2012 |
| WO | 2013010380 A1 | 1/2013 |
| WO | 2013010868 A1 | 1/2013 |
| WO | 2013010869 A1 | 1/2013 |
| WO | 2013027802 A1 | 2/2013 |
| WO | 2013034933 A1 | 3/2013 |

(Continued)

OTHER PUBLICATIONS

Foster, "Deuterium Isotope Effects in Studies of Drug Metabolism", Trends Pharmacal. Sci. 5(12):524 (1984).
Poste et al., "Lipid Vesicles as Carriers for Introducing Biologically Active Materials into Cells", Methods in Cell Biology (Prescott (Ed.)), vol. XIV, p. 33 (1976).
Pietersz et al., "Antibody Conjugates for the Treatment of Cancer", Immunol. Rev., 129:57 (1992).
Rowlinson-Busza et al., "Targeted Delivery of Biologic and other Antineoplastic Agents", Curr. Opin. Oncol., 4:1142 (1992).
International Search Report for International Application No. PCT/US18/019431 dated May 15, 2018 (4 pages).

*Primary Examiner* — John M Mauro

(74) *Attorney, Agent, or Firm* — Venable LLP

(57) ABSTRACT

Inhibitors for Bruton's Tyrosine Kinase (BTK) are disclosed as are compositions thereof, methods for their preparation, and methods for their use.

17 Claims, No Drawings

(56) References Cited

FOREIGN PATENT DOCUMENTS

| WO | 2013052699 A1 | 4/2013 |
| WO | 2013112741 A1 | 8/2013 |
| WO | 2013116562 A1 | 8/2013 |
| WO | 2014047624 A1 | 3/2014 |
| WO | 2014100765 A1 | 6/2014 |
| WO | 2014100767 A1 | 6/2014 |
| WO | 2014201409 A1 | 12/2014 |
| WO | 2015002894 A1 | 1/2015 |
| WO | 2015048689 A1 | 4/2015 |
| WO | 2015181633 A2 | 12/2015 |

OTHER PUBLICATIONS

Written Opinion for International Application No. PCT/US18/019431 dated May 15, 2018 (5 pages).

Trail et al., "Cure of Xenografted Human Carcinomas by BR96-Doxorubicin Immunoconjugates", Science, 261:212 (1993).

* cited by examiner

INHIBITORS OF BRUTON'S TYROSINE KINASE

CROSS-REFERENCE TO RELATED APPLICATION

The applicant claims the benefit under Title 35, United States Code, Section 119(e) of U.S. Provisional Application Ser. No. 62/463,176, filed on Feb. 24, 2017, the disclosure of which is hereby incorporated by reference in its entirety.

FIELD

The present application relates generally to therapeutics and compositions for treating diseases, and more specifically to Bruton's Tyrosine Kinase (BTK) inhibitors.

BACKGROUND

BTK is a member of the Tec family of kinases and involved in signal transduction in B cells and the activation of mast cells. Several compounds have been identified as BTK inhibitors. Examples are disclosed in U.S. Pat. Nos. 7,514,444, 8,501,724, 8,557,803, 8,940,725, 8,940,893, 9,199,997, and 9,371,325; U.S. Pub. Patent App. No. 2014/0142099, PCT Pub. Nos. WO 2008/121742, WO 2013/010380, WO 2013/010868, WO 2013/010869, WO 2015/002894, and WO 2015/048689. Some BTK inhibitors are evaluated as potential therapeutics of, for example, autoimmune diseases and cancers.

There is a need for developing therapeutic agents that inhibit BTK to treat diseases, disorders, or conditions that are mediated by BTK.

BRIEF SUMMARY

In one aspect, the present application provides BTK inhibitors of Formula (I):

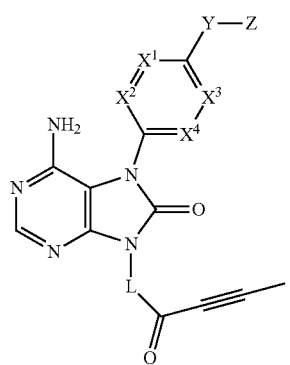

(I)

or a pharmaceutically acceptable salt, isomer, or mixture thereof; wherein:

$X^1$, $X^2$, $X^3$, and $X^4$ are each independently CH or N, with the proviso that no more than two of $X^1$, $X^2$, $X^3$, and $X^4$ are N;

Y is selected from —O—, —NHC(O)—, —C(O)NH—, —NHS(O)$_2$—, and —S(O)$_2$NH—;

Z is selected from 6-membered aryl, 5-membered heteroaryl, and 6-membered heteroaryl; wherein the aryl and heteroaryl motif are each optionally substituted with one, two, or three substituents selected from $C_1$-$C_8$ alkyl, $C_1$-$C_8$ alkoxy, CN, halogen, $C_1$-$C_8$ haloalkyl, NH$_2$, NH($C_1$-$C_8$ alkyl), and N($C_1$-$C_8$ alkyl)$_2$; and L is selected from —$C_3$-$C_6$ cycloalkyl-NH—, —$C_3$-$C_6$ cycloalkyl-N($C_1$-$C_8$alkyl)-,

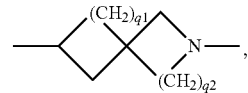

—(CH$_2$)$_{q3}$—NH—, —(CH$_2$)$_{q3}$—N($C_1$-$C_8$ alkyl)-, and wherein q1, q2, and

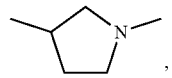

q3 are each independently selected from 1, 2, and 3;

with the proviso that if $X^1$, $X^2$, $X^3$, and $X^4$ are each CH and L is

Y is not O.

In some aspect, L is

In other embodiments, $X^1$, $X^2$, $X^3$, and $X^4$ are each independently CH. In further embodiments, Y is selected from —NHC(O)— and —C(O)NH—. In further embodiments Y is —C(O)NH—. In some embodiments, $X^1$, $X^2$, $X^3$, and $X^4$ are each independently CH, Y is O, and Z is 6-membered aryl. In other embodiments, L is selected from —$C_3$-$C_6$ cycloalkyl-NH— and

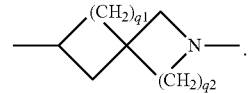

In further embodiments, L is —$C_3$-$C_6$ cycloalkyl-NH—. In further embodiments, L is —$C_6$ cycloalkyl-NH—. In further embodiments, L is

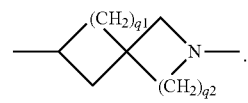

In another aspect, the present application provides BTK inhibitors of Formula (II):

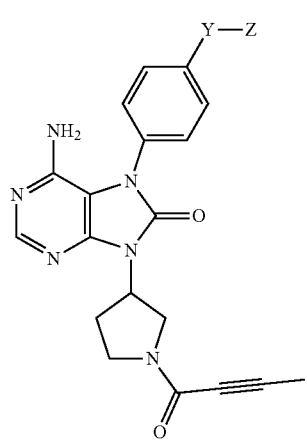

(II)

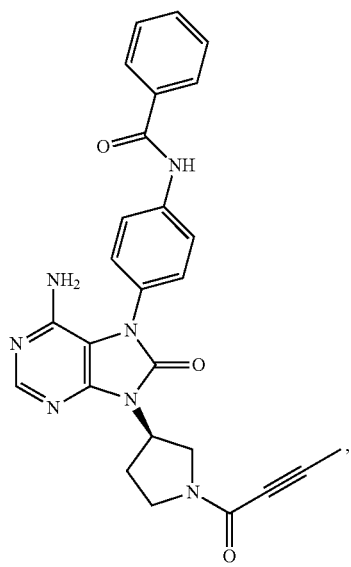

or a pharmaceutically acceptable salt, isomer, or mixture thereof; wherein Y is —NHC(O)— or —C(O)NH—; Z is 6-membered or 5-membered heteroaryl optionally substituted with one, two, or three substituents selected from $C_1$-$C_8$ alkyl, CN, and $C_1$-$C_8$ haloalkyl.

In yet another aspect, the present application provides BTK inhibitors of Formula (III):

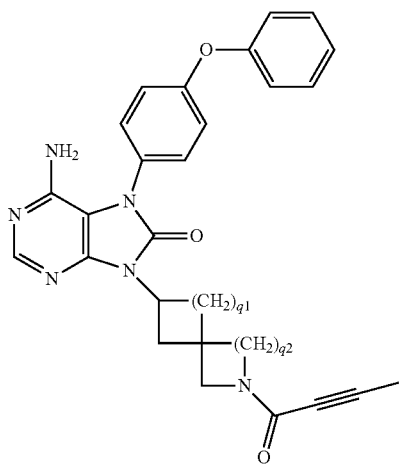

(III)

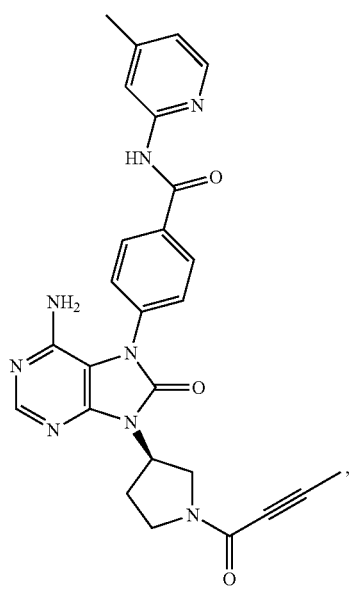

or a pharmaceutically acceptable salt, isomer, or mixture thereof; wherein q1 is 1 and q2 is 1 or 2.

In another aspect, the present application provides the compound selected from the group consisting of:

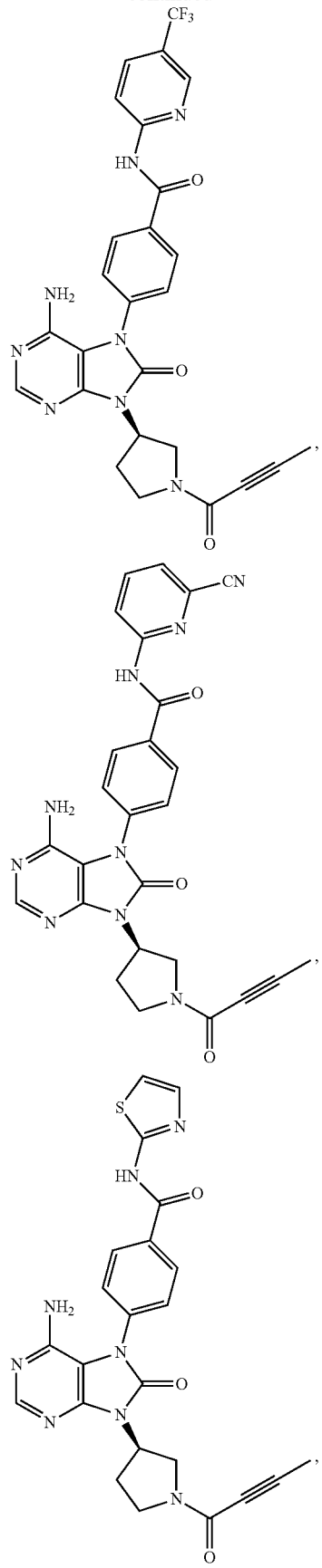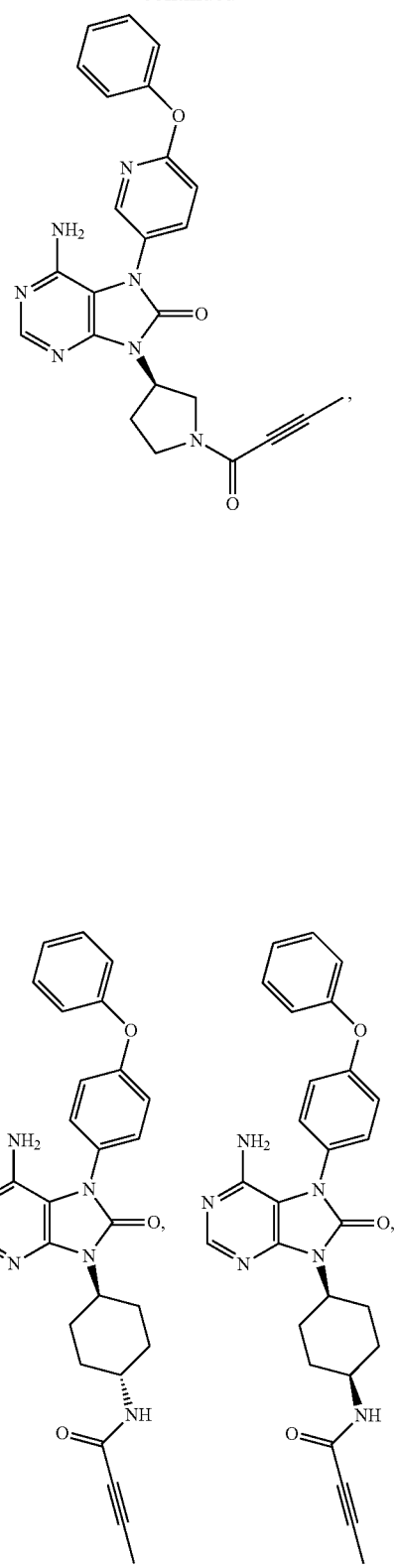

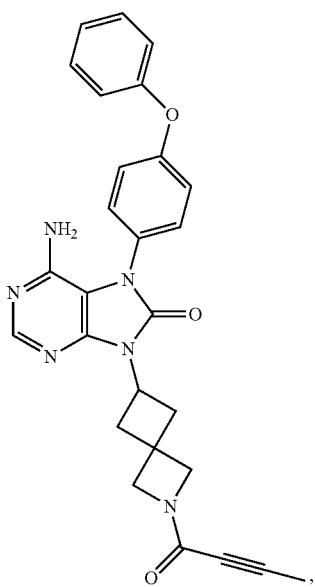

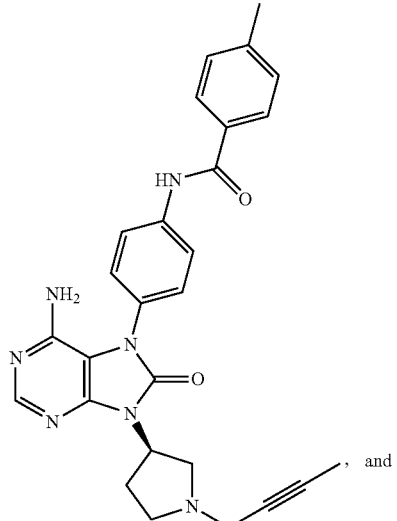

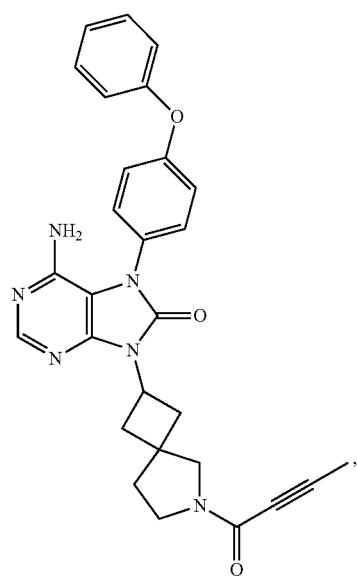

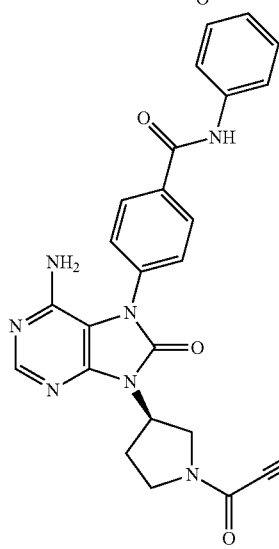

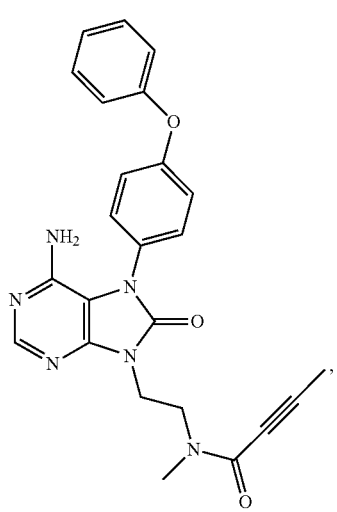

or a pharmaceutically acceptable salt, isomer, or mixture thereof.

In another aspect, provided are the pharmaceutical compositions comprising a BTK inhibitor of Formulae (I)-(III), or a pharmaceutically acceptable salt, isomer, or mixture thereof, and one or more pharmaceutically acceptable carriers or excipients. Also, provided are the articles of manufacture and the unit dosage forms comprising a BTK inhibitor of Formulae (I)-(III) or a pharmaceutically acceptable salt, isomer, or mixture thereof. Additionally provided are the kits comprising a BTK inhibitor of Formulae (I)-(III) or a pharmaceutically acceptable salt, isomer, or mixture thereof, and instructions for use (e.g., instructions for use in BTK-mediated disorder, such as an autoimmune disease or a cancer).

In one aspect, provided are methods of treating a BTK-mediated disorder in a human in need thereof, comprising administering to the human a BTK inhibitor of Formulae (I)-(III) or a pharmaceutically acceptable salt, isomer, or mixture thereof, or compositions comprising a BTK inhibitor of Formulae (I)-(III) or a pharmaceutically acceptable salt, isomer, or mixture thereof. The BTK-mediated disorder, in some embodiments, is an autoimmune disease or a cancer.

Also provided are uses of BTK inhibitors of Formulae (I)-(III) or compositions comprising a BTK inhibitor of Formulae (I)-(III) or a pharmaceutically acceptable salt, isomer, or mixture thereof in the manufacture of medicaments for the treatment of a disease responsive to inhibition of BTK activity, such as an autoimmune disease or a cancer.

Methods of making the BTK inhibitors of Formulae (I)-(III) are provided. Further provided are the methods of producing compositions comprising a BTK inhibitor of Formulae (I)-(III) or a pharmaceutically acceptable salt, isomer, or mixture thereof.

DETAILED DESCRIPTION

The following description is presented to enable a person of ordinary skill in the art to make and use the various embodiments. Descriptions of specific compounds, methods, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but are to be accorded the scope consistent with the claims.

Definitions

As used in the present specification, the following words and phrases are generally intended to have the meanings as set forth below, except to the extent that the context in which they are used indicates otherwise. The term "about" includes and describes the value or parameter per se. For example, "about x" includes and describes "x" per se. In certain embodiment, the term "about" when used in association with a measurement, or used to modify a value, a unit, a constant, or a range of values, refers to variations of +/−1-10%. In some embodiments, the term "about" when used in association with a measurement, or used to modify a value, a unit, a constant, or a range of values, refers to variations of +/−5%. In some embodiments, the term "about" when used in association with a measurement, or used to modify a value, a unit, a constant, or a range of values, refers to variations of +/−10%. The term "between" includes and describes the value or parameter per se. For example, "between x and y" includes and describes "x" and "y" per se. The term "and/or" includes subject matter in the alternative as well as subject matter in combination. For instance, "x, and/or y", includes "x or y" and "x and y".

The term "alkyl" as used herein refers to a straight or branched chain, saturated hydrocarbon having the indicated number of carbon atoms. For example, ($C_1$-$C_8$)alkyl or $C_1$-$C_8$ alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein throughout. The term "substituted alkyl" refers to an alkyl group as defined above, having 1, 2, 3, 4 or 5 substituents, (in some embodiments, 1, 2 or 3 substituents) selected from the group consisting of alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene(—$CH_2$—), ethylene (—$CH_2CH_2$—), the propylene isomers (e.g., —$CH_2CH_2CH_2$— and —$CH(CH_3)CH_2$—), and the like. The term "substituted alkylene" refers to an alkylene group as defined above having 1 to 5 substituents (in some embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like. The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH=$CH_2$), 1-propylene (or allyl, i.e. —$CH_2$CH=$CH_2$), isopropylene (—C($CH_3$)=$CH_2$), and the like. The term "substituted alkenyl" refers to an alkenyl group as defined above having 1 to 5 substituents (in some embodiments, 1, 2 or 3 substituents) as defined for substituted alkyl.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡$CCH_3$), and the like. The term "substituted alkynyl" refers to an alkynyl group as defined above having 1 to 5 substituents (in some embodiments, 1, 2 or 3 substituents) as defined for substituted alkyl.

The term "hydroxyl" or "hydroxy" refers to a group —OH. The term "alkoxy" refers to the group R—O—, where R is alkyl; and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like. The term "substituted alkoxy" refers to the group R—O—, where R is substituted alkyl, where substituted alkyl, substituted alkenyl and substituted alkynyl are as defined herein. The term "thiol" refers to the group —SH. The term "halogen" or "halo" refers to fluoro, bromo, chloro and iodo.

The term "cycloalkyl" refers to cyclic alkyl groups of from 3 to 20 carbon atoms having a single cyclic ring or multiple condensed rings (which may be bridged, spiro, or fused). Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group. Such cycloalkyl groups can optionally be substituted with substituents chosen from the group consisting of alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl. The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like. Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl.

The term "heterocyclyl," "heterocycle," or "heterocyclic" refers to a monoradical saturated group having a single ring or multiple condensed rings (which may be bridged, spiro, or fused), having from 1 to 40 carbon atoms, and from 1 to 10 heteroatoms or 1 to 4 heteroatoms within the ring, each heteroatom independently selected from the group consisting of nitrogen, sulfur, phosphorus, and oxygen. Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl. Examples of heterocyclics include tetrahydrofuranyl, morpholino, piperidinyl, and the like.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy nitrogen containing heteroaryl compounds.

The term "substituted amino" refers to the group —NRR where each R is independently selected from the group consisting of hydrogen, alkyl, cycloalkyl, aryl, heteroaryl and heterocyclyl provided that both R groups are not hydrogen. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl.

"Optional" or "optionally" means that the subsequently described event or circumstance may or may not occur, and that the description includes instances where said event or circumstance occurs and instances in which it does not. A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, an "alkyl-substituted phenyl", where the attachment sites are not explicit, may have any available site of the alkyl group attached to any available site of the phenyl group. In this regard, an "available site" is a site of the group at which a hydrogen of the group may be replaced with a substituent.

A compound of a given formula is intended to encompass the compounds of the disclosure, and the salts, esters, isomers, tautomers, solvates, isotopes, hydrates, forms (including polymorphic, crystal, or co-crystal forms) and prodrugs of such compounds. Additionally, the compounds of the disclosure may possess one or more asymmetric centers, and can be produced as a racemic mixture, a non-racemic mixture, a mixture of diastereoisomers or as individual enantiomers or diastereoisomers. The number of stereoisomers present in any given compound of a given formula depends upon the number of asymmetric centers present (there are 2n stereoisomers possible where n is the number of asymmetric centers). The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated. Compounds of the present disclosure include separable rotational isomers, or atropisomers.

"Isomers" are different compounds that have the same molecular formula. Isomers include stereoisomers, enantiomers and diastereoisomers. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other.

The absolute stereochemistry is specified according to the Cahn Ingold Prelog R S system. When the compound is a pure enantiomer, the stereochemistry at each chiral carbon maybe specified by either R or S. Resolved compounds whose absolute configuration is unknown are designated (+) or (−) depending on the direction (dextro- or laevorotary) that they rotate the plane of polarized light at the wavelength of the sodium D line.

"Tautomers" are structural isomers resulting from the migration of an atom or a functional group within the same organic molecule and lead to a change in one or more of its structural skeleton, electronic density distribution, and chemical properties. It is understood that compounds disclosed herein includes tautomeric forms although not necessarily explicitly shown. In one example, purine may be represented by any of the following tautomers:

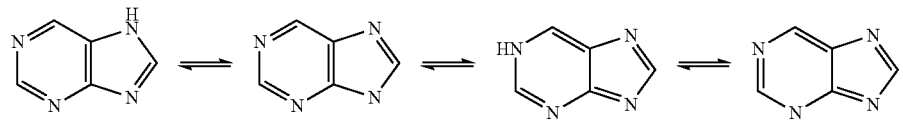 [SMILES: c1ncc2[nH]cnc2n1 ; c1ncc2nc[nH]c2n1 ; c1nc2c[nH]cnc-2n1 ; c1nc2cnc[nH]c-2n1]

Accordingly, a reference to any one of the purine tautomers includes the other tautomeric forms.

If there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereo isomers of it.

The term "solvate" refers to a complex formed by the combining of a compound of any formula as disclosed herein, and a solvent. The term "hydrate" refers to the complex formed by the combining of a compound of any formula disclosed herein, and water.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of any formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half-life of a compound of Formulae (I)-(III), when administered to a mammal. See, for example, Foster, "Deuterium Isotope Effects in Studies of Drug Metabolism", Trends Pharmacal. Sci. 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent in a compound of any formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto. Base addition salts can be prepared from inorganic and organic bases. Salts derived from inorganic bases include, by way of example only, sodium, potassium, lithium, ammonium, calcium and magnesium salts. Further salts derived from organic bases include, but are not limited to, salts of primary, secondary and tertiary amines, such as alkyl amines, dialkyl amines, trialkylamines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroarylamines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. In the general structure $N(R^x)(R^y)(R^z)$, mono-substituted amines have 2 of the three substituents on nitrogen ($R^x$, $R^y$ and $R^z$) as hydrogen; di-substituted amines have 1 of the three substituents on nitrogen ($R^x$, $R^y$ and $R^z$) as hydrogen; and tri-substituted amines have none of the three substituents on nitrogen ($R^x$, $R^y$ and $R^z$) as hydrogen. $R^x$, $R^y$ and $R^z$ may be selected from a variety of substituents such as hydrogen, optionally substituted alkyl, aryl, heteroayl, cycloalkyl, cycloalkenyl, heterocyclyl and the like. The abovementioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to NH(heteroaryl)$_2$, wherein "heteroaryl" is as defined herein and so on.

Acid addition salts may be prepared from inorganic and organic acids. Acid addition salts may be prepared from inorganic acids such as hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, ethane-1,2-disulfonic acid, naphthalene-1,5-disulfonic acid, p-toluene-sulfonic acid, salicylic acid, and the like.

In some embodiments, a salt is a "pharmaceutically acceptable salt". A pharmaceutically acceptable salt of a given compound refers to salts that retain the biological effectiveness and properties of a given compound, and which are not biologically or otherwise undesirable. See: P. Heinrich Stahl and Camille G. Wermuth (Eds.) Pharmaceutical Salts: Properties, Selection, and Use (International Union of Pure and Applied Chemistry), Wiley-VCH; 2nd revise Edition (May 16, 2011).

Compounds described herein may be presented in the form of chemical structures or names. The compounds shown below in Table 1 are named using ChemBioDraw Ultra 10.0 and it should be understood that other names may be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Applied Chemistry (IUPAC). The naming and numbering of the compounds of the present disclosure is illustrated with representative compounds shown in Table 1 below.

Inhibitors of Bruton's Tyrosine Kinase (BTK)

The present application provides the compounds inhibit BTK activities, suitable as BTK inhibitors. In one aspect, the BTK inhibitor have the structure of Formula (I):

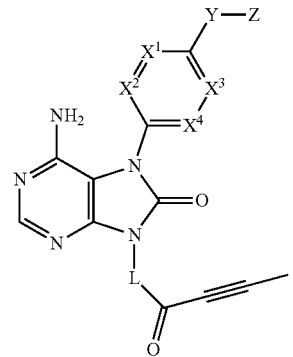

or a pharmaceutically acceptable salt, isomer, or mixture thereof; wherein:

$X^1$, $X^2$, $X^3$, and $X^4$ are each independently CH or N;

Y is selected from —O—, —NHC(O)—, —C(O)NH—, —NHS(O)$_2$—, and —S(O)$_2$NH—;

Z is selected from aryl and heteroaryl, wherein the aryl or heteraryl motif is optionally substituted with one, two, or three members selected from alkyl, alkoxy, CN, halogen, haloalkyl, $NH_2$, NH-alkyl, and N-(alkyl)$_2$; and L is selected from alkyl, heterocyclyl, and cycloalkyl, wherein the heterocyclyl or cycloalkyl motif is optionally substituted with one, two, or three members selected from alkyl, alkoxy, CN, halogen, haloalkyl, $NH_2$, NH-alkyl, and N-(alkyl)$_2$.

In certain embodiment, $X^1$, $X^2$, $X^3$, and $X^4$ are each independently CH or N, with the proviso that no more than two of $X^1$, $X^2$, $X^3$, and $X^4$ are N;

Y is selected from —O—, —NHC(O)—, —C(O)NH—, —NHS(O)$_2$—, and —(O)$_2$NH—;

Z is selected from 6-membered aryl, 5-membered heteroaryl, and 6-membered heteroaryl; wherein the aryl or heteroaryl motif is optionally substituted with one, two, or three members selected from $C_1$-$C_8$ alkyl, $C_1$-$C_8$ alkoxy, CN, halogen, $C_1$-$C_8$ haloalkyl, $NH_2$, NH($C_1$-$C_8$ alkyl), and N($C_1$-$C_8$ alkyl)$_2$; and L is selected from —$C_3$-$C_6$ cycloalkyl-NH—, —$C_3$-$C_6$ cycloalkyl-N($C_1$-$C_3$ alkyl)-,

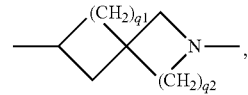

—(CH$_2$)$_{q3}$—NH—, —(CH$_2$)$_{q3}$—N($C_1$-$C_3$ alkyl)-,

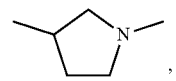

and wherein q1, q2, and q3 are each independently selected from 1, 2, and 3;

with the proviso that if $X^1$, $X^2$, $X^3$, and $X^4$ are each CH and L is

Y is not O.

In some embodiments, $X^1$, $X^2$, $X^3$, and $X^4$ are each independently CH. In some other embodiments, $X^1$ is N and $X^2$, $X^3$, and $X^4$ are each independently CH. In other embodiments, Y is selected from —NHC(O)— and —C(O)NH—. In some other embodiments, Y is —C(O)NH—. In certain other embodiments, Y is selected from —NHC(O)—.

In certain embodiments, Z is selected from 6-membered aryl, 5-membered heteroaryl, and 6-membered heteroaryl; wherein the aryl or heteroaryl motif is optionally substituted with one, two, or three members or substituents selected from $C_1$-$C_8$ alkyl, $C_1$-$C_8$ alkoxy, CN, halogen, $C_1$-$C_3$ haloalkyl, $NH_2$, $NH(C_1$-$C_8$ alkyl), and $N(C_1$-$C_8$ alkyl)$_2$. In certain other embodiments, Z is 6-membered aryl substituted with one substituent selected from $C_1$-$C_8$ alkyl, $C_1$-$C_8$ alkoxy, CN, halogen, $C_1$-$C_8$ haloalkyl, $NH_2$, $NH(C_1$-$C_8$ alkyl), and $N(C_1$-$C_8$ alkyl)$_2$. In some other embodiments, Z is 5-membered or 6-membered heteroaryl substituted with one substituent selected from $C_1$-$C_8$ alkyl, $C_1$-$C_8$ alkoxy, CN, halogen, $C_1$-$C_8$ haloalkyl, $NH_2$, $NH(C_1$-$C_8$ alkyl), and $N(C_1$-$C_8$ alkyl)$_2$. In additional embodiment, Z is selected from phenyl, thiazolyl, and pyridinyl, wherein each of phenyl, thiazolyl, and pyridinyl is optionally substituted with $C_1$-$C_8$ alkyl, $C_1$-$C_8$ alkoxy, CN, halogen, or $C_1$-$C_8$ haloalkyl. In some additional embodiment, Z is selected from phenyl, thiazolyl, and pyridinyl. In certain additional embodiment, Z is selected from phenyl, thiazolyl, and pyridinyl, wherein each of phenyl, thiazolyl, and pyridinyl is substituted with $C_1$-$C_8$ alkyl, $C_1$-$C_8$ alkoxy, CN, halogen, or $C_1$-$C_8$ haloalkyl. In yet additional embodiment, Z is selected from phenyl, thiazolyl, and pyridinyl, wherein each of phenyl, thiazolyl, and pyridinyl is optionally substituted with methyl, ethyl, propyl, butyl, CN, or fluoromethyl, difluoromethyl, trifluoromethyl, fluoroethyl, difluoroethyl, trifluorethyl, fluoropropyl, difluoropropyl, or trifluoropropyl. In other additional embodiments, Z is selected from phenyl, thiazolyl, pyridinyl, pyridinyl substituted with one member selected from methyl, trifluoromethyl, and CN.

In other embodiments, L is selected from $C_3$-$C_6$ alkyl, $C_3$-$C_8$ heterocyclyl, and $C_3$-$C_8$ cycloalkyl, wherein the alkyl, heterocyclyl or cycloalkyl motif is optionally substituted with one, two, or three members selected from $C_1$-$C_8$ alkyl, $C_1$-$C_8$ alkoxy, CN, halogen, $C_1$-$C_8$ haloalkyl, $NH_2$, NH—$C_1$-$C_8$ alkyl, and N—($C_1$-$C_8$ alkyl)$_2$. In some other embodiments, L is selected from —$C_3$-$C_6$ cycloalkyl-, —$C_3$-$C_6$ cycloalkyl-NH— and

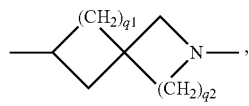

each of which is optionally substituted with $C_1$-$C_8$ alkyl; wherein q1 and q2 are each independently selected from 1, 2, and 3. In some embodiments, L is

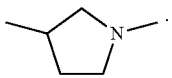

In further embodiments, L is —$C_3$-$C_6$ cycloalkyl-NH—. In some further embodiments, L is

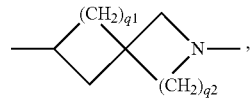

wherein q1 is 1 and q2 is 1. In certain further embodiments, L is

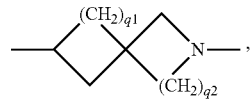

wherein q1 is 1 and q2 is 2. In yet further embodiment, L is —(CH$_2$)$_{q3}$—N(C$_1$-C$_3$ alkyl)-, wherein q3 is 2.

It is understood that each of the above definition may be combined with each other. By way of example, in other embodiments, the BTK inhibitors have the structure of Formula (I), wherein $X^1$, $X^2$, $X^3$, and $X^4$ are each independently CH, Y is O, and Z is phenyl. In some other embodiments, the BTK inhibitors have the structure of Formula (I), wherein $X^1$, $X^2$, $X^3$, and $X^4$ are each independently CH, Y is —NHC(O)—, and Z is phenyl. In some other embodiments, the BTK inhibitors have the structure of Formula (I), wherein $X^1$, $X^2$, $X^3$, and $X^4$ are each independently CH, Y is Y is —C(O)NH—, and Z is thiazolyl or pyridinyl, each of which is optionally substituted with one member selected from $C_1$-$C_8$ alkyl, CN, $C_1$-$C_3$ haloalkyl. In certain other embodiments, the BTK inhibitors have the structure of Formula (I), wherein $X^1$, $X^2$, $X^3$, and $X^4$ are each independently CH or N, with the proviso that one of $X^1$, $X^2$, $X^3$, and $X^4$ is N, Y is —C(O)NH—, and Z is pyridinyl optionally substituted with one substituent selected from $C_1$-$C_8$ alkyl, CN, $C_1$-$C_8$ haloalkyl.

In another embodiment, the BTK inhibitors have the structure of Formula (II):

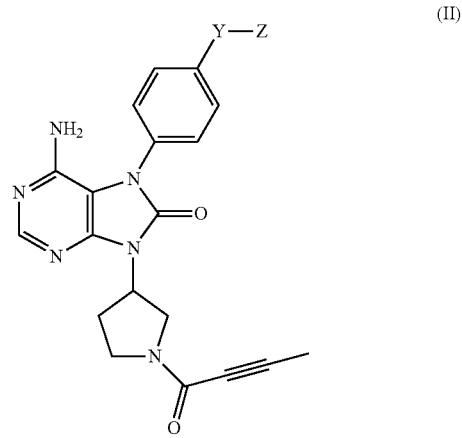

(II)

or a pharmaceutically acceptable salt, isomer, or mixture thereof; wherein Y and Z are defined above. In some embodiment, the BTK inhibitors have the structure of Formula (II), wherein Y is —NHC(O)— or —C(O)NH—; and Z is 6-membered or 5-membered heteroaryl optionally substituted with one, two, or three substituents selected from $C_1$-$C_8$ alkyl, CN, and $C_1$-$C_8$ haloalkyl. In some other embodiments, Y is —NHC(O)— or —C(O)NH—; Z is 6-membered or 5-membered heteroaryl substituted with one substituent selected from $C_1$-$C_8$ alkyl, CN, and $C_1$-$C_8$ haloalkyl. In other embodiment, the BTK inhibitors have the structure of Formula (II), wherein Y is —NHC(O)—, and Z is phenyl. In some other embodiment, the BTK inhibitors have the structure of Formula (II), wherein Y is —C(O)NH—, and Z is thiazolyl or pyridinyl optionally substituted with one member selected from methyl, trifluoromethyl, and CN.

In another embodiment, the BTK inhibitors have the structure of Formula (II-a):

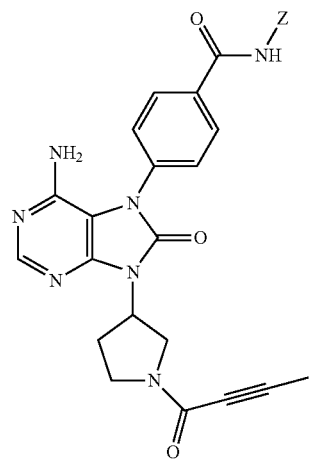

(II-a)

or a pharmaceutically acceptable salt, isomer, or mixture thereof; wherein Y and Z are defined above. In some other embodiment, the BTK inhibitors have the structure of Formula (II-a), wherein Z is thiazolyl, pyridinyl, or pyridinyl substituted with one member selected from methyl, trifluoromethyl, and CN.

In another embodiment, the BTK inhibitors have the structure of Formula (II-b):

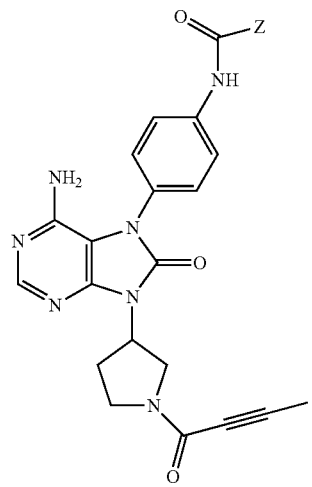

(II-b)

or a pharmaceutically acceptable salt, isomer, or mixture thereof; wherein Y and Z are defined above. In other embodiment, the BTK inhibitors have the structure of Formula (II-b), wherein Z is phenyl.

In yet another embodiment, the BTK inhibitors have the structure of Formula (III):

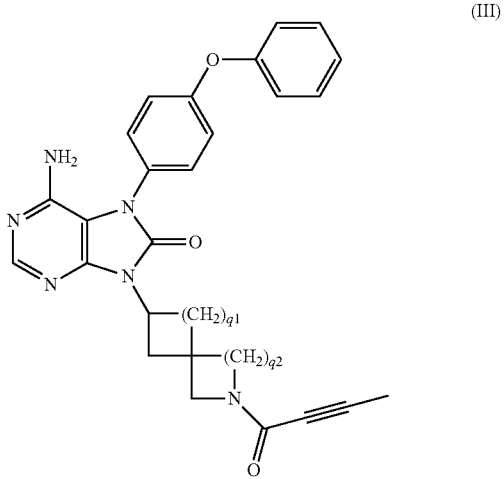

(III)

or a pharmaceutically acceptable salt, isomer, or mixture thereof; wherein q1 and q2 are defined above. In one embodiment, the BTK inhibitors have the structure of Formula (III), wherein q1 is 1 and q2 is 1 or 2.

In certain embodiments, the BTK inhibitors of Formulae (I)-(III) have the following structures in Table 1.

TABLE 1

Inhibitors of Bruton's Tyrosine Kinase of Formulae (I)-(III).

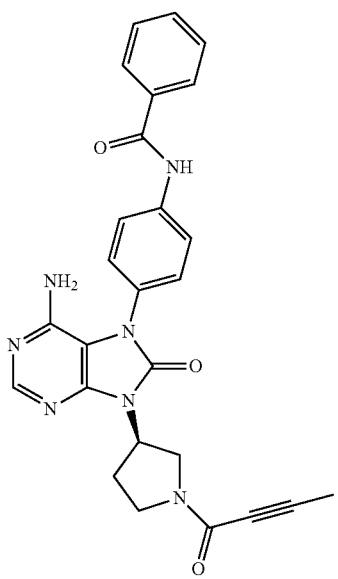 [SMILES: CC#CC(=O)N1CC[C@@H](n2c(=O)n(-c3ccc(NC(=O)c4ccccc4)cc3)c3c(N)ncnc32)C1]

(R)-N-(4-(6-amino-9-(1-but-2-ynoylpyrrolidin-3-yl)-8-oxo-8,9-dihydro-7H-purin-7-yl)phenyl)benzamide TABLE 1-continued Inhibitors of Bruton's Tyrosine Kinase of Formulae (I)-(III).

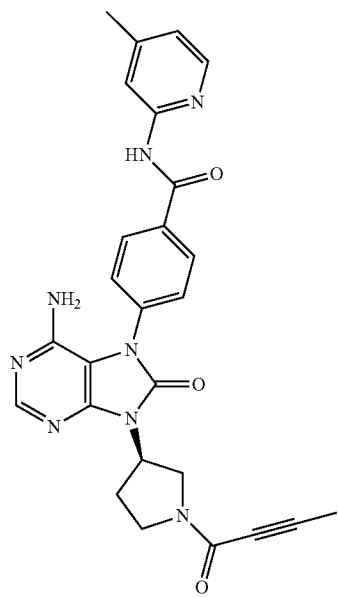 [SMILES: CC#CC(=O)N1CC[C@@H](n2c(=O)n(-c3ccc(C(=O)Nc4cc(C)ccn4)cc3)c3c(N)ncnc32)C1]

(R)-4-(6-amino-9-(1-but-2-ynoylpyrrolidin-3-yl)-
8-oxo-8,9-dihydro-7H-purin-7-yl)-N-(4-
methylpyridin-2-yl)benzamide

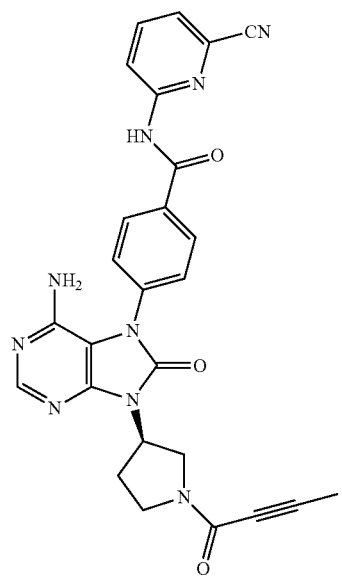

(R)-4-(6-amino-9-(1-but-2-ynoylpyrrolidin-3-yl)-
8-oxo-8,9-dihydro-7H-purin-7-yl)-N-(6-
cyanopyridin-2-yl)benzamide

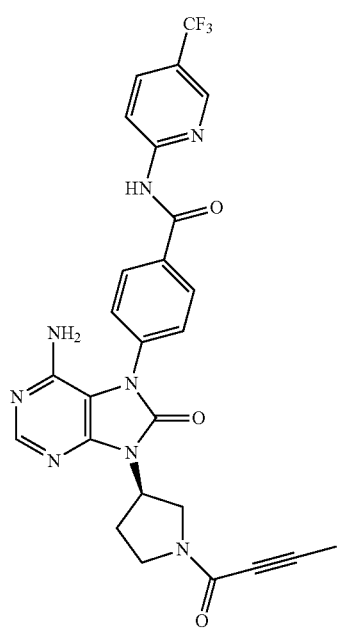 [SMILES: CC#CC(=O)N1CC[C@@H](n2c(=O)n(-c3ccc(C(=O)Nc4ccc(C(F)(F)F)cn4)cc3)c3c(N)ncnc32)C1]

(R)-4-(6-amino-9-(1-but-2-ynoylpyrrolidin-3-
yl)-8-oxo-8,9-dihydro-7H-purin-7-yl)-N-(5-
(trifluoromethyl)pyridin-2-yl)benzamide

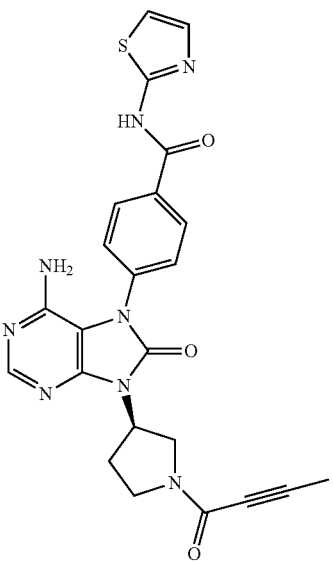 [SMILES: CC#CC(=O)N1CC[C@@H](n2c(=O)n(-c3ccc(C(=O)Nc4nccs4)cc3)c3c(N)ncnc32)C1]

(R)-4-(6-amino-9-(1-but-2-ynoylpyrrolidin-3-
yl)-8-oxo-8,9-dihydro-7H-purin-7-yl)-N-
(thiazol-2-yl)benzamide TABLE 1-continued
Inhibitors of Bruton's Tyrosine Kinase of Formulae (I)-(III).
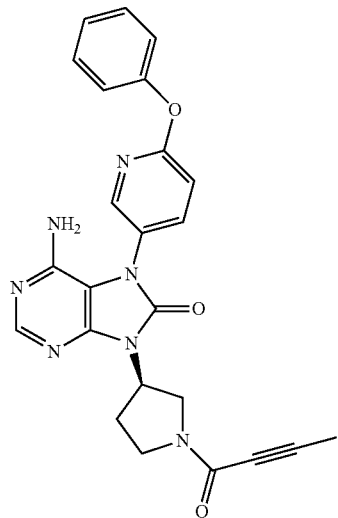 [SMILES: CC#CC(=O)N1CC[C@@H](n2c(=O)n(-c3ccc(Oc4ccccc4)nc3)c3c(N)ncnc32)C1]
(R)-6-amino-9-(1-but-2-ynoylpyrrolidin-3-yl)-7-
(6-phenoxypyridin-3-yl)-7H-purin-8(9H)-one
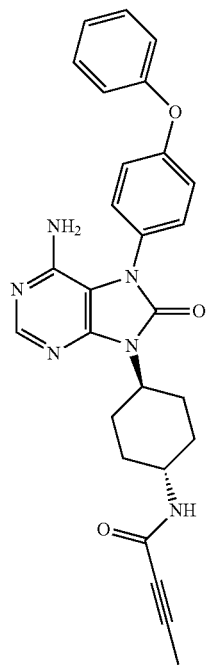 [SMILES: CC#CC(=O)N[C@H]1CC[C@H](n2c(=O)n(-c3ccc(Oc4ccccc4)cc3)c3c(N)ncnc32)CC1]
N-(trans-4-(6-amino-8-oxo-7-(4-
phenoxyphenyl)-7H-purin-9(8H)-
yl)cyclohexyl)but-2-ynamide
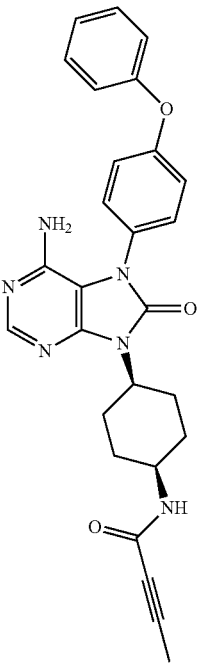 [SMILES: CC#CC(=O)N[C@H]1CC[C@@H](n2c(=O)n(-c3ccc(Oc4ccccc4)cc3)c3c(N)ncnc32)CC1]
N-(cis-4-(6-amino-8-oxo-7-(4-phenoxyphenyl)-
7H-purin-9(8H)-yl)cyclohexyl)but-2-ynamide
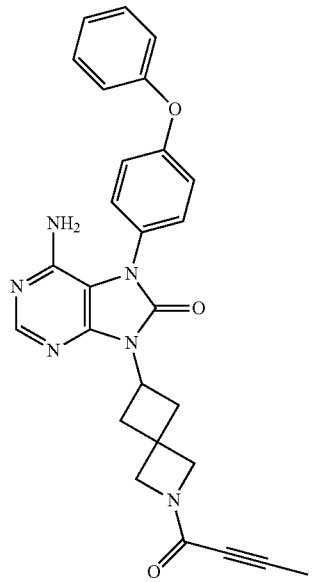 [SMILES: CC#CC(=O)N1CC2(CC(n3c(=O)n(-c4ccc(Oc5ccccc5)cc4)c4c(N)ncnc43)C2)C1]
6-amino-9-(2-but-2-ynoyl-2-
azaspiro[3.3]heptan-6-yl)-7-(4-
phenoxyphenyl)-7H-purin-8(9H)-one TABLE 1-continued Inhibitors of Bruton's Tyrosine Kinase of Formulae (I)-(III).

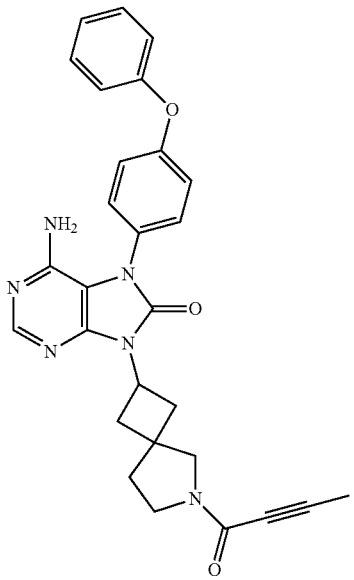 [SMILES: CC#CC(=O)N1CCC2(CC(n3c(=O)n(-c4ccc(Oc5ccccc5)cc4)c4c(N)ncnc43)C2)C1]

6-amino-9-(6-but-2-ynoyl-6-azaspiro[3.4]octan-
2-yl)-7-(4-phenoxyphenyl)-7H-purin-8(9H)-one

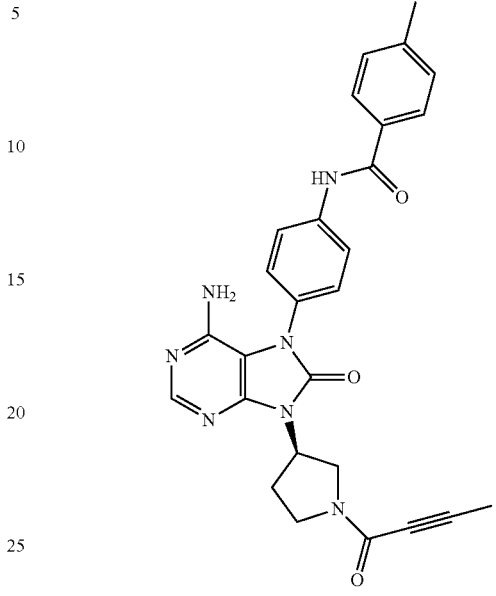

(R)-N-(4-(6-amino-9-(1-but-2-ynoylpyrrolidin-3-
yl)-8-oxo-8,9-dihydro-7H-purin-7-yl)phenyl)-4-
methylbenzamide

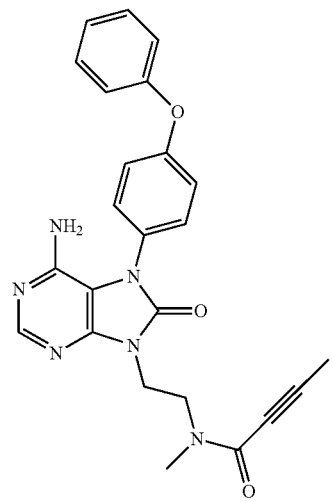 [SMILES: CC#CC(=O)N(C)CCn1c(=O)n(-c2ccc(Oc3ccccc3)cc2)c2c(N)ncnc21]

N-(2-(6-amino-8-oxo-7-(4-phenoxyphenyl)-
7H-purin-9(8H)-yl)ethyl)-N-methylbut-2-
ynamide

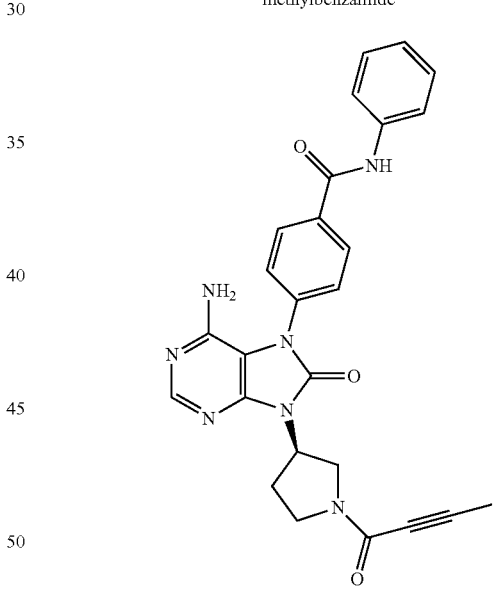

(R)-4-(6-amino-9-(1-but-2-ynoylpyrrolidin-3-
yl)-8-oxo-8,9-dihydro-7H-purin-7-yl)-N-
phenylbenzamide The compounds of the present application have BTK inhibitory activity and as a result may be useful as agents for preventing and/or treating BTK-related diseases, i.e., diseases in which B cells and/or mast cells participate, for example, allergic diseases, autoimmune diseases, inflammatory diseases, thromboembolic diseases, cancers, and graft-versus host diseases. Without being bound to any hypothesis, the compounds of the present application may exhibit selective inhibition on B cell activation and may be effective as inhibitors of B cell activation.

Compositions

In some embodiments, the compositions described herein may comprise a substantially pure BTK inhibitor of Formulae (I)-(III), or a pharmaceutically acceptable salt, isomer, or mixture thereof, or may be substantially free of impurities. In some embodiments, the term "substantially pure" or "substantially free" with respect to a particular BTK inhibitor of Formulae (I)-(III) means that the composition comprising the BTK inhibitor of Formulae (I)-(III) contains less than 95%, less than 90%, less than 80%, less than 70%, less than 65%, less than 60%, less than 55%, less than 50%, less than 40%, less than 30%, less than 20%, less than 15%, less than 10%, less than 5%, or less than 1% by weight of other substances, including impurities. In certain embodiments, "substantially pure" or "substantially free of" refers to a substance free of other substances, including impurities. Impurities may, for example, include by-products or left over reagents from chemical reactions, contaminants, degradation products, water, and solvents.

The BTK inhibitors of Formulae (I)-(III), or a pharmaceutically acceptable salt, isomer, or mixture thereof, may be administered as the neat chemical, but it is typical, and preferable, to administer the compound in the form of a composition or formulation, such as a pharmaceutical composition or formulation. Accordingly, provided are pharmaceutical compositions comprising a BTK inhibitor of Formulae (I)-(III), or a pharmaceutically acceptable salt, isomer, or mixture thereof, and one or more pharmaceutically acceptable carriers, excipients, or other ingredients (including inert solid diluents and fillers, diluents, including sterile aqueous solution and various organic solvents, permeation enhancers, solubilizers and adjuvants). The compositions may include a BTK inhibitor of Formulae (I)-(III), or a pharmaceutically acceptable salt, isomer, or mixture thereof, either as the sole active agent or in combination with other agents, such as oligo- or polynucleotides, oligo- or polypeptides, drugs, or hormones mixed with one or more pharmaceutically acceptable carriers, excipients, or other ingredients. Carriers, excipients, and other ingredients may be deemed pharmaceutically acceptable insofar as they are compatible with other ingredients of the formulation and not deleterious to the recipient thereof.

Provided herein are pharmaceutical compositions comprising a BTK inhibitor of Formulae (I)-(III), or a pharmaceutically acceptable salt, isomer, or mixture thereof, and a pharmaceutical acceptable carrier or excipient. Techniques for formulation and administration of pharmaceutical compositions can be found in Remington's Pharmaceutical Sciences, 18th Ed., Mack Publishing Co, Easton, Pa., 1990. The pharmaceutical compositions described herein may be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation may be determined by one of skill in the art depending on the route of administration and the desired dosage. Such formulations may influence the physical state, stability, rate of in vivo release, and rate of in vivo clearance of the administered agent. Depending on the condition being treated, these pharmaceutical compositions may be formulated and administered systemically or locally.

The pharmaceutical compositions may be formulated to contain suitable pharmaceutically acceptable carriers, and optionally can comprise excipients and auxiliaries that facilitate processing of BTK inhibitors of Formulae (I)-(III), or a pharmaceutically acceptable salt, isomer, or mixture thereof, into preparations that may be used pharmaceutically. The mode of administration generally determines the nature of the carrier. For example, formulations for parenteral administration may include aqueous solutions of the active compounds in water-soluble form. Carriers suitable for parenteral administration may be selected from among saline, buffered saline, dextrose, water, and other physiologically compatible solutions. Preferred carriers for parenteral administration are physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art. For preparations including proteins, the formulation can include stabilizing materials, such as polyols (e.g., sucrose) and/or surfactants (e.g., nonionic surfactants), and the like.

Alternatively, formulations for parenteral use may include dispersions or suspensions of a BTK inhibitor of Formulae (I)-(III), or a pharmaceutically acceptable salt, isomer, or mixture thereof, prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions may contain substances that increase the viscosity of the suspension, such as sodium carboxymethylcellulose, sorbitol, dextran, and mixtures thereof. Optionally, the suspension also may contain suitable stabilizers or agents that increase the solubility of the compounds to allow for the preparation of highly concentrated solutions. Aqueous polymers that provide pH-sensitive solubilization and/or sustained release of the active agent also may be used as coatings or matrix structures, e.g., methacrylic polymers, such as the EUDRAGIT® series available from Rohm America Inc. (Piscataway, N.J.). Emulsions, e.g., oil-in-water and water-in-oil dispersions, also may be used, optionally stabilized by an emulsifying agent or dispersant (surface active materials; surfactants). Suspensions can contain suspending agents such as ethoxylated isostearyl alcohols, polyoxyethlyene sorbitol and sorbitan esters, microcrystalline cellulose, aluminum metahydroxide, bentonite, agar-agar, gum tragacanth, and mixtures thereof.

Liposomes containing the BTK inhibitors of Formulae (I)-(III), or a pharmaceutically acceptable salt, isomer, or mixture thereof, also may be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See, e.g., Prescott (Ed.), Methods in Cell Biology, Vol. XIV, p. 33, Academic Press, New York (1976).

In some embodiments, BTK inhibitors of Formulae (I)-(III), or a pharmaceutically acceptable salt, isomer, or mixture thereof, or compositions thereof disclosed herein are formulated for oral administration using pharmaceutically acceptable carriers, excipients or other ingredients well known in the art. Preparations formulated for oral administration may be in the form of tablets, pills, capsules, cachets, dragees, lozenges, liquids, gels, syrups, slurries, elixirs, suspensions, or powders. To illustrate, pharmaceutical preparations for oral use may be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Preferred oral formulations include tablets, dragees, and gelatin capsules. These preparations may contain one or more excipients, which include, without limitation:

a) diluents, such as microcrystalline cellulose and sugars, including lactose, dextrose, sucrose, mannitol, or sorbitol;

b) binders, such as sodium starch glycolate, croscarmellose sodium, magnesium aluminum silicate, starch from corn, wheat, rice, potato, etc.;

c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;

d) disintegrating or solubilizing agents such as crosslinked polyvinyl pyrrolidone, starches, agar, alginic acid or a salt thereof, such as sodium alginate, or effervescent compositions;

e) lubricants, such as silica, talc, stearic acid or its magnesium or calcium salt, and polyethylene glycol;

f) flavorants and sweeteners;

g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers. In some embodiment, provided are tablets comprising a BTK inhibitor of Formulae (I)-(III) and one or more pharmaceutically acceptable carriers or excipients.

Gelatin capsules include push-fit capsules made of gelatin, as well as soft, sealed capsules made of gelatin and a coating such as glycerol or sorbitol. Push-fit capsules may contain the active ingredient mixed with fillers, binders, lubricants, and/or stabilizers, etc. In soft capsules, the active compounds may be dissolved or suspended in suitable fluids, such as fatty oils, liquid paraffin, or liquid polyethylene glycol with or without stabilizers. Dragee cores may be provided with suitable coatings such as concentrated sugar solutions, which also may contain gum arabic, talc, polyvinyl pyrrolidone, carbopol gel, polyethylene glycol, and/or titanium dioxide, lacquer solutions, and suitable organic solvents or solvent mixtures.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, or ampoule). The BTK inhibitors of Formulae (I)-(III) are effective over a wide dosage range and are generally administered in a pharmaceutically effective amount. It will be understood, however, that the amount of BTK inhibitor of Formulae (I)-(III) actually administered will be determined by a physician, in the light of the relevant circumstances, including the condition to be treated, the chosen route of administration, the age, weight, and response of the subject receiving such treatment, the severity of the subject's symptoms, and the like.

The tablets or pills described herein may be coated or otherwise compounded to provide a dosage form affording the advantage of prolonged action, or to protect from the acid conditions of the stomach. For example, the tablet or pill may comprise an inner dosage and an outer dosage element, the latter being in the form of an envelope over the former. The two elements may be separated by an enteric layer that serves to resist disintegration in the stomach and permit the inner element to pass intact into the duodenum or to be delayed in release. A variety of materials may be used for such enteric layers or coatings, such materials including a number of polymorphic acids and mixtures of polymorphic acids with such materials as shellac, cetyl alcohol, and cellulose acetate.

For example, provided are unit dosages comprising a BTK inhibitor of Formulae (I)-(III). Exemplary unit dosage levels of BTK inhibitors of Formulae (I)-(III) for a human subject may, in certain variations, be between about 0.01 mg to about 1000 mg, between about 1 mg to about 200 mg, between about 10 mg to about 200 mg, between about 20 mg to about 160 mg, between about 10 mg to about 100 mg, between about 50 mg to about 175 mg, between about 20 mg to about 150 mg, between about 75 mg to about 100 mg, or between about 100 mg to about 200 mg. Individual doses of BTK inhibitors of Formulae (I)-(III) that may be administered to a human in need thereof include individual doses of 1 mg, 5 mg, 10 mg, 20 mg, 30 mg, 40 mg, 50 mg, 60 mg, 70 mg, 75 mg, 80 mg, 90 mg, 100 mg, 110 mg, 120 mg, 130 mg, 140 mg, 150 mg, 160 mg, 170 mg, 175 mg, and 200 mg. The doses of the BTK inhibitors of Formulae (I)-(III) may be administered as determined by a medical professional and may be administered once daily or may be delivered twice daily, three times daily, or four times daily. In one embodiment, the BTK inhibitor of Formulae (I)-(III) is administered orally, once a day, to a subject in need thereof at a dose of 20 mg, 40 mg, 80 mg, or 150 mg. In some embodiment, the BTK inhibitor of Formulae (I)-(III) is administered orally, twice a day, to a subject at a dose of 20 mg, 40 mg, or 75 mg. In additional embodiment, the therapeutically effective amount of the BTK inhibitor described herein is a dose of from about 1 mg to about 200 mg. In another embodiment, the BTK inhibitor described herein is administered at a dose of from about 10 mg to about 200 mg. In another embodiment, the BTK in a human is administered at a dose of from about 20 mg to about 160 mg. In other embodiment, the BTK inhibitor is administered to a human at a dose of: a) from about 10 mg to about 100 mg, b) from about 50 mg to about 175 mg, c) from about 20 mg to about 150 mg, d) from about 75 mg to about 100 mg, and e) from about 100 mg to about 200 mg. Individual doses of the BTK inhibitor that may be administered to a human in need thereof include individual doses of 1 mg, 5 mg, 10 mg, 20 mg, 30 mg, 40 mg, 50 mg, 60 mg, 70 mg, 75 mg, 80 mg, 901 mg, 100 mg, 110 mg, 120 mg, 130 mg, 140 mg, 150 mg, 160 mg, 170 mg, 175 mg, and 200 mg. The doses of the BTK inhibitor may be administered as determined by a medical professional and may be administered once daily or may be delivered twice daily, three times daily, or four times daily. In one embodiment, the method of the present application comprises administering a BTK inhibitor of Formulae (I)-(III) or a composition thereof at a dose of 10 mg, 20 mg, 40 mg, 80 mg, 150 mg, or 200 mg daily. In other embodiment, the method of the present application comprises administering a BTK inhibitor of Formulae (I)-(III) or a composition thereof at a dose of 20 mg, 40 mg, 80 mg, or 150 mg daily.

Modes of Administration and Dosages

Pharmaceutical compositions including a BTK inhibitor of Formulae (I)-(III) may be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral, buccal, sublingual, and rectal administration. Transepithelial administration modalities include, for example, transmucosal administration and transdermal administration. Transmucosal administration includes, for example, enteral administration as well as nasal, inhalation, and deep lung administration; vaginal administration; and buccal and sublingual administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT™.

Moreover, the therapeutic index of the BTK inhibitor of Formulae (I)-(III) may be enhanced by modifying or derivatizing the compound for targeted delivery to cancer cells expressing a marker that identifies the cells as such. For example, the compound may be linked to an antibody that recognizes a marker that is selective or specific for cancer cells, so that the compounds are brought into the vicinity of the cells to exert their effects locally, as previously described. See e.g., Pietersz et al., Immunol. Rev., 129:57 (1992); Trail et al., Science, 261:212 (1993); and Rowlinson-Busza et al., Curr. Opin. Oncol., 4:1142 (1992). Tumor-directed delivery of the compound can enhance the therapeutic benefit by, inter alfa, minimizing potential nonspecific toxicities that can result from radiation treatment or chemotherapy. In some embodiments, the BTK inhibitor of Formulae (I)-(III) and radioisotopes or chemotherapeutic agents may be conjugated to the same anti-tumor antibody.

Pharmacokinetic and pharmacodynamic information relating to a BTK inhibitor of Formulae (I)-(III) and a formulation of a BTK inhibitor of Formulae (I)-(III) may be collected through preclinical in vitro and in vivo studies, later confirmed in humans during the course of clinical trials. Thus, for a BTK inhibitor of Formulae (I)-(III) used in the methods described herein, a therapeutically effective dose may be estimated initially from biochemical and/or cell-based assays. Then, dosage may be formulated in animal models to achieve a desirable circulating concentration range that modulates BTK expression or activity. As human studies are conducted further information will emerge regarding the appropriate dosage levels and duration of treatment for various diseases and conditions.

Toxicity and therapeutic efficacy of such compounds may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies may be used in formulating a range of dosage for human use. The dosage of such compounds lies preferably within a range of circulating concentrations that include the $ED_{50}$ with little or no toxicity.

It should be understood that any effective administration regimen regulating the timing and sequence of doses may be used. A BTK inhibitor of Formulae (I)-(III) and pharmaceutical compositions thereof may include those wherein the active ingredient is administered in an effective amount to achieve its intended purpose. In some embodiments, a "therapeutically effective amount" means an amount sufficient to modulate BTK expression or activity, including, and thereby treat a subject (e.g., a human) suffering an indication, or to alleviate the existing symptoms of the indication.

Exemplary dosage levels for a human subject are of the order of from about 0.001 milligram of active agent per kilogram body weight (mg/kg) to about 1000 mg/kg. Typically, dosage units of the active agent comprise from about 0.01 mg to about 1000 mg, preferably from about 0.1 mg to about 100 mg, depending upon the indication, route of administration, and severity of the condition, for example. Depending on the route of administration, a suitable dose can be calculated according to body weight, body surface area, or organ size. The final dosage regimen may be determined by the attending physician in view of good medical practice, considering various factors that modify the action of drugs, e.g., the specific activity of the compound, the identity and severity of the disease state, the responsiveness of the subject, the age, condition, body weight, sex, and diet of the subject, and the severity of any infection. Additional factors that may be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages may be ascertained through use of established assays for determining concentration of the agent in a body fluid or other sample together with dose response data.

The frequency of dosing depends on the pharmacokinetic parameters of the agent and the route of administration. Dosage and administration are adjusted to provide sufficient levels of the active moiety or to maintain the desired effect. Accordingly, the pharmaceutical compositions may be administered in a single dose, multiple discrete doses, continuous infusion, sustained release depots, or combinations thereof, as required to maintain desired minimum level of the agent. Short-acting pharmaceutical compositions (i.e., short half-life) may be administered once a day or more than once a day (e.g., two, three, or four times a day). Long acting pharmaceutical compositions might be administered every 3 to 4 days, every week, or once every two weeks.

Uses of the BTK Inhibitors

Provided are uses of BTK inhibitors of Formulae (I)-(III) or compositions thereof described herein to selectively or specifically inhibit BTK activity therapeutically or prophylactically. The method comprises administering a BTK inhibitor of Formulae (I)-(III) or compositions thereof to a subject (e.g., a human) in need thereof in an amount sufficient to inhibit BTK activity. The method may be employed to treat humans or animals suffering from, or subject to, a condition whose symptoms or pathology is mediated by BTK expression or activity.

"Treatment" or "treating" is an approach for obtaining beneficial or desired results including clinical results. Beneficial or desired clinical results may include one or more of the following:

(i) decreasing one more symptoms resulting from the disease;

(ii) diminishing the extent of the disease and/or stabilizing the disease (e.g., delaying the worsening of the disease);

(iii) delaying the spread (e.g., metastasis) of the disease;

(iv) delaying or slowing the recurrence of the disease and/or the progression of the disease;

(v) ameliorating the disease state and/or providing a remission (whether partial or total) of the disease and/or decreasing the dose of one or more other medications required to treat the disease;

(vi) increasing the quality of life, and/or (vii) prolonging survival.

In some embodiments, "disorder" is intended to encompass medical disorders, diseases, conditions, syndromes, and the like, without limitation. The methods disclosed in the application embrace various modes of treating a subject, including but is not limited to an animal, a mammal, a primate, and a human. Among the mammalian animals that may be treated are, for example, humans; companion animals (pets), including dogs and cats; farm animals, including cattle, horses, sheep, pigs, and goats; laboratory animals, including rats, mice, rabbits, guinea pigs, and nonhuman primates; and zoo specimens. Among the non-mammalian animals that may be treated include, for example, birds, fish, reptiles, and amphibians. In certain embodiment, the method described herein may be employed for a human in need thereof.

In one aspect, the BTK inhibitors of Formulae (I)-(III) and compositions thereof described herein may be employed in methods of inhibiting the growth or proliferation of cancer cells of hematopoietic origin, such as cancer cells. In some embodiments, the cancer cells are of lymphoid origin, and in specific embodiments, the cancer cells are related to or derived from B lymphocytes or B lymphocyte progenitors. In another aspect, the BTK inhibitors of Formulae (I)-(III) and compositions thereof described herein may be employed in methods of treating a human with a cancer.

Cancers amenable to treatment using the method disclosed in the application include, for example, non-Hodgkin's lymphomas, among which B-cell non-Hodgkin's lymphomas are particularly suitable, for example, Burkitt's lymphoma, AIDS-related lymphoma, marginal zone B-cell lymphoma (nodal marginal zone B-cell lymphoma, extranodal marginal zone B-cell lymphoma, and splenic marginal zone B-cell lymphoma), diffuse large B-cell lymphoma, primary effusion lymphoma, lymphomatoid granulomatosis, follicular lymphoma, B-cell chronic lymphocytic leukemia, B-cell prolymphocytic leukemia, lymphoplasmacytic leukemia/Waldenstrom's macroglobulinemia, plasmacytoma, mantle cell lymphoma, mediastinal large B-cell lymphoma, intravascular large B-cell lymphoma, and hairy cell leukemia. In addition to non-Hodgkin's lymphoma, the cancers may be amenable to treatment by the present application include pancreatic endocrine tumors, for example, insulinoma, gastrinoma, glucagonoma, somatostatinoma, VIPoma, PPoma, and GRFoma. Other cancer cells, of hematopoietic origin or otherwise, that express BTK also can be treated by administration of the BTK inhibitors of Formulae (I)-(III) and compositions thereof described herein.

In another aspect, the BTK inhibitors of Formulae (I)-(III) and compositions thereof described herein can be employed in methods of treating an autoimmune disease. In particular embodiments, the autoimmune disease is inflammatory bowel disease, arthritis, lupus, rheumatoid arthritis, psoriatic arthritis, osteoarthritis, Still's disease, juvenile arthritis, type I diabetes, myasthenia gravis, Hashimoto's thyroiditis, Ord's thyroiditis, Basedow's disease, Sjögren's syndrome, multiple sclerosis, Guillain-Barré syndrome, acute disseminated encephalomyelitis, Addison's disease, opsoclonus-myoclonus syndrome, ankylosing spondylitis, anti-phospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu's arteritis, temporal arteritis, warm autoimmune hemolytic anemia, Wegener's granuloma, psoriasis, alopecia universalis, Behget's disease, chronic fatigue syndrome, dysautonomia, endometriosis, interstitial cystitis, myotonia, vulvodynia, and systemic lupus erythematosus.

In yet another aspect, provided are methods of treating a human having a BTK-mediated disorder by administering a BTK inhibitor of Formulae (I)-(III) to the human. Provided are also methods of modulating BTK an individual by administering a BTK inhibitor of Formulae (I)-(III). In one variation, the human has cancer, such as leukemia or lymphoma. In another variation, the human has an autoimmune disease, such as asthma, rheumatoid arthritis, multiple sclerosis, or lupus.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein, an antibody-drug conjugate (ADC), a radiotherapeutic agent, an anti-neoplastic agent, an anti-proliferation agent, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, or any combination thereof. These therapeutic agents may be in the forms of compounds, antibodies, polypeptides, or polynucleotides. In one embodiment, the application provides a product comprising a compound described herein and an additional therapeutic agent as a combined preparation for simultaneous, separate, or sequential use in therapy, e.g. a method of treating a disease, disorder, or condition that is mediated by BTK.

The one or more therapeutic agents include, but are not limited to, an inhibitor, agonist, antagonist, ligand, modulator, stimulator, blocker, activator or suppressor of a gene, ligand, receptor, protein, factor such as: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5), chemokine (C—X—C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COPS signalosome subunit 5, CSF-1 (colony-stimulating factor 1 receptor), CSF2 gene, CTLA-4 (cytotoxic T-lymphocyte protein 4) receptor, Cyclin D1, Cyclin G1, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid×receptor (FXR), Fas ligand, Fatty acid synthase, Ferritin, FGF-2 ligand, FGF-5 ligand, fibroblast growth factor (FGF, such as FGF1, FGF2, FGF4), Fibronectin, Fms-related tyrosine kinase 3 (Flt3), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releaseing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha, Imprinted Maternally Expressed Transcript (H19) gene, mitogen-activated protein kinase kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KISS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mc1-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1, 2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase)gene, Rosl tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Specific protein 1 (Sp 1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-f3 receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor or any combination thereof.

One aspect provides the methods of treating a human having a BTK-mediated disorder by administering a BTK inhibitor of Formulae (I)-(III) to the human in combination with one or more other therapeutic agents selecting from the group of an apoptosis signal-regulating kinase (ASK) inhibitor, a discoidin domain receptor (DDR) inhibitor, a histone deacetylase (HDAC) inhibitor, a Janus kinase (JAK) inhibitor, a lysyl oxidase-like protein 2 (LOXL2) inhibitor, a matrix metalloprotease 9 (MMP9) inhibitor, a phosphatidylinositol 3-kinase (PI3K) inhibitor, a spleen tyrosine kinase (SYK) inhibitor, a BET-bromodomain 4 (BRD4) inhibitor, a checkpoint inhibitor, a B-cell chronic lymphocytic leukemia (CLL)/lymphoma 2 (BCL-2) inhibitor and a CD20 inhibitor. In any of the foregoing methods, the BTK inhibitors of Formulae (I)-(III) may be administered to the individual as a unit dosage, for example in the form of a tablet, as described herein. Also, in any of the foregoing methods, the BTK inhibitors of Formulae (I)-(III) and one or more therapeutic agents may be administered simultaneously or sequentially.

Examples of one or more therapeutic agents include, but are not limited to, ASK inhibitors include ASK1 inhibitors as those described in WO 2011/008709 and WO 2013/112741; CD47 inhibitors such as anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621; CDK inhibitors such as abemaciclib, alvocidib (HMR-1275, flavopiridol), AT-7519, FLX-925, LEE001, palbociclib, ribociclib, rigosertib, selinexor, UCN-01, and TG-02; DDR inhibitors such as those disclosed in PCT Pub. Nos. WO 2014/047624, WO 2013/027802, and WO 2013/034933, U.S. Pub. Patent App. No. 2011/0287011 and 2009/0142345; HDAC inhibitors such as abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), vorinostat; IDOL inhibitors such as BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST; JAK inhibitors such as AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019; LOXL inhibitors such as the antibodies described in WO 2009/017833, WO 2009/035791, and WO 2011/097513; MMP9 inhibitors such as marimastat (BB-2516), cipemastat (Ro 32-3555) and those described in PCT Pub. No. WO 2012/027721; MEK inhibitors such as antroquinonol, binimetinib, cobimetinib (GDC-0973, XL-518), MT-144, selumetinib (AZD6244), sorafenib, trametinib (GSK1120212), uprosertib+trametinib; PI3K inhibitors such as ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, IPI-549, KAR4141, LY294002, LY3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in PCT Pub. Nos. WO 2005/113556, WO 2013/052699, WO 2013/116562, WO 2014/100765, WO 2014/100767, and WO 2014/201409; SYK inhibitors such as 6-(1H-indazol-6-yl)-N-(4-morpholinophenyl)imidazo [1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 and U.S. Pub. Patent App. No. 2015/0175616; TLR8 inhibitors such as E-6887, IMO-4200, IMO-8400, IMO-9200, MCT-465, MEDI-9197, motolimod, resiquimod, VTX-1463, and VTX-763; TLR9 inhibitors such as IMO-2055, IMO-2125, lefitolimod, litenimod, MGN-1601, and PUL-042; TKIs inhibitors such as afatinib, ARQ-087, asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, midostaurin, nintedanib, ODM-203, osimertinib (AZD-9291), ponatinib, poziotinib, quizartinib, radotinib, rociletinib, sulfatinib (HMPL-012), sunitinib, and TH-4000.

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above. Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors. Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®). Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®). Examples of anti-androgens include apalutamide, abiraterone, enzalutamide, flutamide, galeterone, nilutamide, bicalutamide, leuprolide, goserelin, ODM-201, APC-100, ODM-204. Examples of progesterone receptor antagonist include onaprostone.

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, $\alpha,\alpha'$-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456; 5,059,714; 5,120,764; 5,182,297; and 5,252,608 relating to 2-(1-naphthyloxymemyl)-3-fluoroallylamine, and U.S. Pub. Patent App. No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone. Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamideethyl)dithio)butanoic acid, p-2-amino-3-methyl-3-((2-aminoethyl)dithio)butanoic acid, sodium-4-((p-1-dimethyl-2-amino-2-carboxyethyl)dithio) butane sulphurate, 2-acetamideethyl-2-acetamideethanethiol sulphanate, and sodium-4-mercaptobutanesulphinate trihydrate.

The immunotherapeutic agents include and are not limited to therapeutic antibodies suitable for treating patients. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, 3F8, and the like. Rituximab can be used for treating indolent B-cell cancers, including marginal-zone lymphoma, WM, CLL and small lymphocytic lymphoma. A combination of Rituximab and chemotherapy agents is especially effective. The exemplified therapeutic antibodies may be further labeled or combined with a radioisotope particle such as indium-111, yttrium-90 (90Y-clivatuzumab), or iodine-131. It is understood that, the agents, molecules, compounds, or antibodies described above may have additional mode of mechanism and would not be limited to the mode described above; for example, a chemotherapy agent may be an anti-fibrotic agent.

Additionally provided are uses of the BTK inhibitors of Formulae (I)-(III) in the manufacture of a drug product. The BTK inhibitors of Formulae (I)-(III) may serve as intermediates in the manufacturing process to produce the drug product.

Articles of Manufacture and Kits

Compositions comprising a BTK inhibitor of Formulae (I)-(III) and formulated in one or more pharmaceutically acceptable carriers, excipients or other ingredients may be prepared, placed in an appropriate container, and labeled for treatment of an indicated condition. Accordingly, there also are contemplated articles of manufacture, such as containers comprising dosage forms of a BTK inhibitor of Formulae (I)-(III) and labels containing instructions for use of the compound.

In some embodiments, the articles of manufacture are containers comprising dosage forms of a BTK inhibitor of Formulae (I)-(III) and one or more pharmaceutically acceptable carriers, excipients or other ingredients. In one embodiment of the articles of manufacture described herein, the dosage form is a tablet.

Kits also are contemplated. For example, a kit comprises a dosage form of a pharmaceutical composition and a package insert containing instructions for use of the composition in treatment of a medical condition. The instructions for use in the kit may be for treating a BTK-mediated disorder, including, for example, an autoimmune disease or a cancer. In certain embodiments, conditions indicated on the label can include, for example, treatment of an autoimmune disease or a cancer.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

Preparation of the Inhibitors of Bruton's Tyrosine Kinase of Formulae (I)-(III)

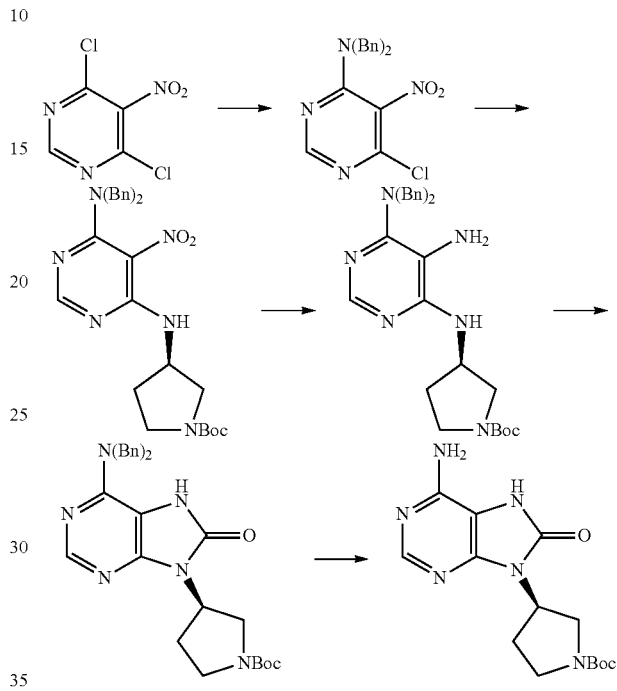

Synthesis of (R)-tert-butyl 3-(6-amino-8-oxo-7H-purin-9(8H)-yl)pyrrolidine-1-carboxylate Step 1—Synthesis of N,N-dibenzyl-6-chloro-5-nitropyrimidin-4-amine To a stirred solution of 4,6-dichloro-5-nitropyrimidine (1.0 eq) and triethylamine (3 eq) in DCM (5 mL/mmol) at about 0° C. under nitrogen was added bisbenzylamine (1.0 eq) in DCM (0.5 mL/mmol) dropwise over about 2 hrs. Stirring was continued for about 30 min before the reaction mixture was diluted with water (2.5 mL/mmol). The layers were separated and the aqueous layer was extracted with DCM (3×2.5 mL/mmol). The combined organic layers were washed with water (2×1.5 mL/mmol) and brine (1.5 mL/mmol), dried over sodium sulfate and concentrated in vacuo to give the title compound. LC-MS: 355.0 [M+1]$^+$. $^1$H NMR (400 MHz, CDCl$_3$): δ 8.46 (s, 1H), 7.34 (d, J=7.6 Hz, 6H), 7.20-7.07 (m, 4H), 4.66 (s, 4H).

Step 2—Synthesis of (R)-tert-butyl 3-(6-(dibenzylamino)-5-nitropyrimidin-4-ylamino)pyrrolidine-1-carboxylate To a solution of N,N-dibenzyl-6-chloro-5-nitropyrimidin-4-amine (1.0 eq) and tert-butyl (3R)-3-aminopyrrolidine-1-carboxylate (1.05 eq) in dioxane (1 mL/mmol) was added triethylamine (1.2 eq). The mixture was stirred at about 50° C. for about 5 hours. The reaction mixture was cooled to room temperature, and the solvent was concentrated. The residue was diluted with water (2.5 mL/mmol) and extracted with ethyl acetate (3×2.5 mL/mmol). The organic layers were washed with brine, then dried over anhydrous sodium sulfate, and concentrated. The residue was purified by flash silica gel column chromatography to obtain the title compound. LC-MS: 505.3 [M+1]⁺

Step 3—Synthesis of (R)-tert-butyl 3-(5-amino-6-(dibenzylamino)pyrimidin-4-ylamino)pyrrolidine-1-carboxylate To a mixture of (R)-tert-butyl 3-(6-(dibenzylamino)-5-nitropyrimidin-4-ylamino)pyrrolidine-1-carboxylate (1.0 eq) and zinc powder (10 eq) in ethyl acetate (10 mL/mmol) in an ice bath was added aqueous solution of ammonium chloride (3.0 M, 2 mL/mmol). The temperature was raised to room temperature. After being stirred for about 2 hours, the reaction mixture was filtered through a pad of Celite. The filtrate was concentrated. The residue was purified by flash silica gel column chromatography to obtain the title compound. LC-MS: 505.3 [M+1]⁺

Step 4-Synthesis of (R)-tert-butyl 3-(6-(dibenzy-lamino)-8-oxo-7H-purin-9(8H)-yl)pyrrolidine-1-carboxylate A solution of (R)-tert-butyl 3-(5-amino-6-(dibenzylamino)pyrimidin-4-ylamino)pyrrolidine-1-carboxylate (1.0 eq) and 1,1'-carbonyl diimidazole (2.0 eq) in tetrahydrofuran (7 mL/mmol) was stirred at about 60° C. for about 15 hours. The mixture was concentrated and diluted with water, extracted with ethyl acetate. The organic layer was washed with brine, and dried over anhydrous sodium sulfate, and concentrated. The residue was purified by flash silica gel column chromatography (PE/EA, 2/1~1/1) to afford the title compound. LC-MS: 501.35 [M+1]⁺

Step 5—Synthesis of (R)-tert-butyl 3-(6-amino-8-oxo-7H-purin-9(8H)-yl)pyrrolidine-1-carboxylate A mixture of tert-butyl 3-(6-(dibenzylamino)-8-oxo-7H-purin-9(8H)-yl)pyrrolidine-1-carboxylate (1.0 eq) and 10 percent Pd(OH)₂ on carbon (0.05 g/mmol) in glacial acetic acid (2 mL/mmol) under hydrogen atmosphere was stirred at about 80° C. overnight. The reaction mixture was filtered through a pad of Celite, and washed with ethyl acetate. The filtrate was concentrated in vacuum and the residue was basified with saturated sodium bicarbonate solution. The aqueous layer was extracted with dichloromethane. The combined organic layers were dried over sodium sulfate and concentrated to obtain the title compound. LC-MS: 362.2 [M+41]⁺. ¹H NMR (400 MHz, CDCl₃) δ 10.45 (s, 1H), 8.19 (d, J=14.1 Hz, 1H), 5.64 (s, 2H), 5.04 (s, 1H), 4.04-3.92 (m, 1H), 3.74 (d, J=11.0 Hz, 2H), 3.51-3.37 (m, 1H), 2.79 (d, J=11.0 Hz, 1H), 2.21 (s, 1H), 1.47 (d, J=12.5 Hz, 9H).

Example 1—Synthesis of (R)—N-(4-(6-amino-9-(1-but-2-ynoylpyrrolidin-3-yl)-8-oxo-8,9-dihydro-7H-purin-7-yl)phenyl)benzamide

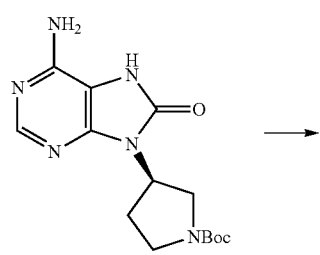

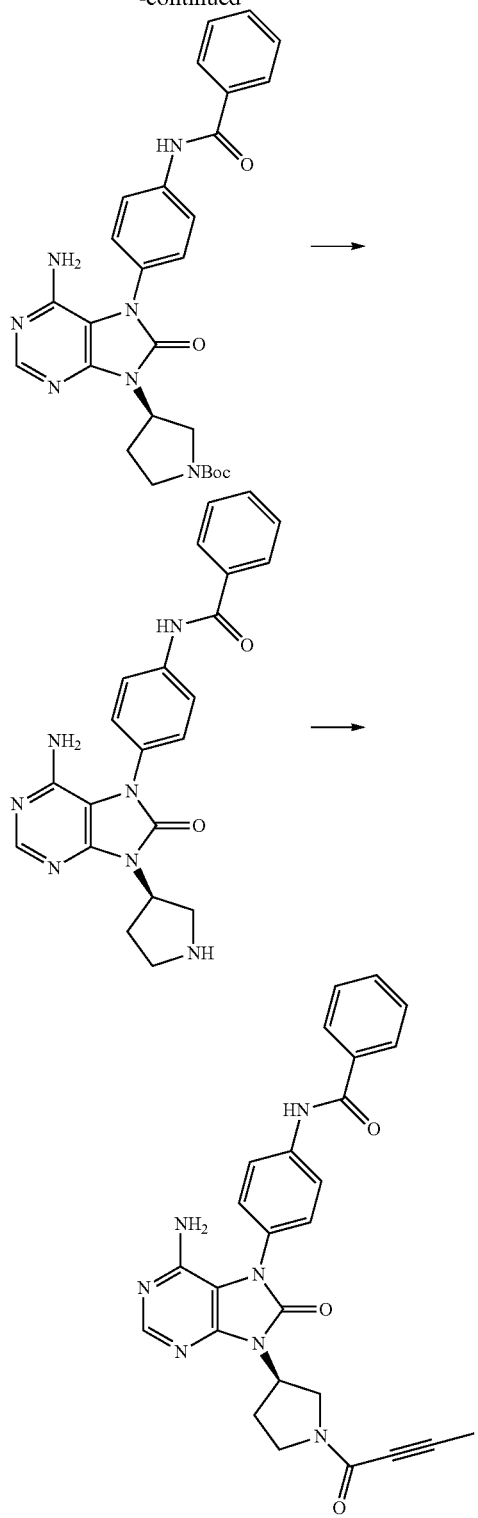

Step 1—Synthesis of (R)-tert-butyl 3-(6-amino-7-(4-benzamidephenyl)-8-oxo-7H-purin-9(8H)-yl)pyrrolidine-1-carboxylate To a suspension of (R)-tert-butyl 3-(6-amino-8-oxo-7H-purin-9(8H)-yl)pyrrolidine-1-carboxylate (1.0 eq) and 4-benzamidephenylboronic acid (3.0 eq) in dichloromethane (10 mL/mmol) was added copper(II) acetate (2.0 eq) followed by pyridine (3.0 eq). The mixture was stirred at about 35° C. overnight. The reaction mixture was filtered through a pad of Celite. The filtrate was diluted with ethyl acetate and washed with water and brine. The organic phase was separated, dried over sodium sulfate, and concentrated to dryness. The residue was purified by flash column chromatography (silica, hexanes/ethyl acetate 1:1 to dichloromethane/methanol 10:1) to give the title compound. LC-MS: 516 [M+H]$^+$.

Step 2—Synthesis of (R)—N-(4-(6-amino-8-oxo-9-(pyrrolidin-3-yl)-8,9-dihydro-7H-purin-7-yl)phenyl) benzamide (R)-tert-Butyl 3-(6-amino-7-(4-benzamidephenyl)-8-oxo-7H-purin-9 (8H)-yl)pyrrolidine-1-carboxylate was treated with HCl/dioxane (4.0 M, 7 mL/mmol) at room temperature for about 1 h. The reaction was concentrated to dryness. The residue was used for the next step without further purification. LC-MS: m/z=416 [M+H]$^+$.

Step 3—Synthesis of (R)—N-(4-(6-amino-9-(1-but-2-ynoylpyrrolidin-3-yl)-8-oxo-8,9-dihydro-7H-purin-7-yl)phenyl)benzamide To a solution (R)—N-(4-(6-amino-8-oxo-9-(pyrrolidin-3-yl)-8,9-dihydro-7H-purin-7-yl)phenyl)benzamide (1.0 eq) and 2-butynoic acid (1.2 eq) in DMF (10 mL/mmol) was added HATU (1.2 eq) followed by the addition of DIPEA (3.0 eq) at room temperature for about 10 min. The mixture was diluted with ethyl acetate and washed with water. The organic phase was separated, dried with sodium sulfate, and concentrated to dryness. The residue was purified by prep-HPLC (C18) (H$_2$O/MeCN, +0.1% HCO$_2$H, 95/5 to 0/100 gradient within 30 min) to give the title compound. $^1$H NMR (300 MHz, CD$_3$OD) δ 8.15 (s, 1H), 7.96-7.92 (m, 4H), 7.61-7.48 (m, 5H), 5.27-5.22 (m, 1H), 4.32-4.30 (m, 0.5H), 4.15-4.06 (m, 1.5H), 3.91-3.82 (m, 1.5H), 3.57-3.53 (m, 0.5H), 2.82-2.75 (m, 1H), 2.40-2.36 (m, 1H), 2.06 (d, 3H).

Example 2—Synthesis of (R)-4-(6-amino-9-(1-but-2-ynoylpyrrolidin-3-yl)-8-oxo-8,9-dihydro-7H-purin-7-yl)-N-(4-methylpyridin-2-yl)benzamide

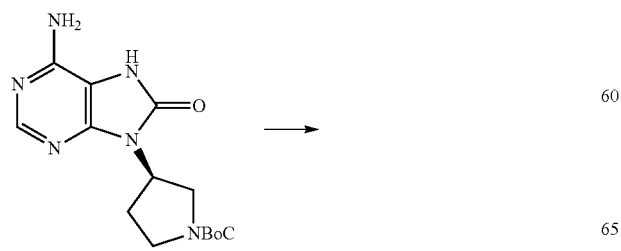

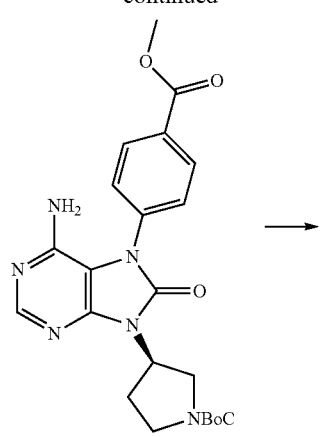

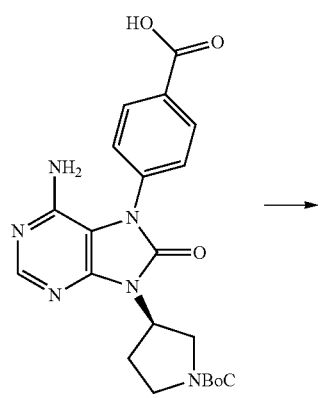

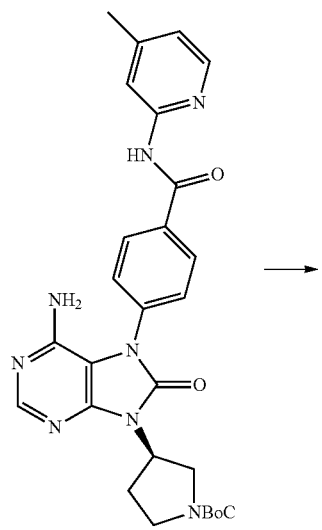

49
-continued

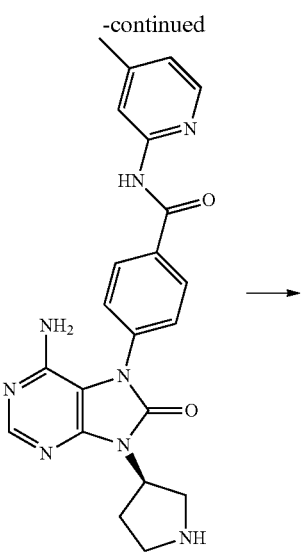

→

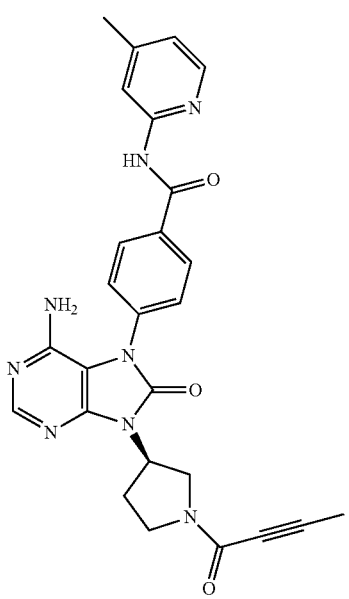

Step 1—Synthesis of (R)-tert-butyl 3-(6-amino-7-(4-(methoxycarbonyl)phenyl)-8-oxo-7H-purin-9(8H)-yl)pyrrolidine-1-carboxylate To a suspension of (R)-tert-butyl 3-(6-amino-8-oxo-7H-purin-9(8H)-yl)pyrrolidine-1-carboxylate (1.0 eq) and 4-(methoxycarbonyl)phenylboronic acid (1.5 eq) in dichloromethane (5 mL/mmol) was added copper(II) acetate (3.0 eq) followed by pyridine (6.0 eq). The mixture was stirred at about 35° C. overnight. The reaction mixture was filtered through a pad of Celite. The filtrate was diluted with ethyl acetate and washed with water. The organic phase was dried over sodium sulfate, and concentrated to dryness. The residue was purified by flash column chromatography (silica, hexanes/ethyl acetate=1:1 to dichloromethane/methanol=10:1) followed by prep-HPLC (C18) chromatography (H$_2$O/MeCN, +0.1% HCO$_2$H, 95/5 to 0/100 gradient within 30 min) to give the title compound. LC-MS: 455 [M+H]$^+$.

50

Step 2-Synthesis of (R)-4-(6-amino-9-(1-(tert-butoxycarbonyl)pyrrolidin-3-yl)-8-oxo-8,9-dihydro-7H-purin-7-yl)benzoic acid To a solution of (R)-tert-butyl 3-(6-amino-7-(4-(methoxycarbonyl)phenyl)-8-oxo-7H-purin-9(8H-1)-yl)pyrrolidine-1-carboxylate (1.0 eq) in THF/MeOH (2:1, 8.5 mL/mmol) was added lithium hydroxide (2.0 eq). The mixture was stirred at room temperature for about 2 h and neutralized to pH about 4-5 with 1 N HCl. The precipitate was filtered and dried to give the title compound. LC-MS: 441 [M+H]$^+$.

Step 3-Synthesis of (R)-tert-butyl 3-(6-amino-7-(4-(4-methylpyridin-2-ylcarbamoyl)phenyl)-8-oxo-7H-purin-9(8H)-yl)pyrrolidine-1-carboxylate To a solution of (R)-4-(6-amino-9-(1-(tert-butoxycarbonyl)pyrrolidin-3-yl)-8-oxo-8,9-dihydro-7H-purin-7-yl)benzoic acid (1.0 eq) and 2-amino-3-methylpyridine (3.0 eq) in DMF (23 mL/mmol) was added HATU (2.0 eq) and DIPEA (5.0 eq). The mixture was stirred at about 40° C. overnight. The reaction was quenched with methanol and concentrated to dryness. The residue was diluted with ethyl acetate and washed with water. The organic phase was separated, dried over sodium sulfate, and concentrated to dryness. The residue was purified by C-18 prep-HPLC (H$_2$O/MeCN, +0.1% HCO$_2$H, 95/5 to 0/100 gradient within 30 min) to give the title compound. LC-MS: 531 [M+H]$^+$.

Step 4-Synthesis of ((R)-4-(6-amino-8-oxo-9-(pyrrolidin-3-yl)-8,9-dihydro-7H-purin-7-yl)-N-(4-methylpyridin-2-yl)benzamide (R)-tert-butyl 3-(6-amino-7-(4-(4-methylpyridin-2-ylcarbamoyl)phenyl)-8-oxo-7H-purin-9(8H-1)-yl)pyrrolidine-1-carboxylate was treated with HCl/dioxane (4.0 M, 24 mL/mmol) at room temperature for about 1 h. The reaction was concentrated to dryness. The residue was purified by prep-HPLC (C-18) chromatography (H$_2$O/MeCN+0.1% HCO$_2$H 95/5 to 0/100 gradient within 30 min) to give the title compound. LC-MS: 431 [M+H]$^+$.

Step 5-Synthesis of (R)-4-(6-amino-9-(1-but-2-ynoylpyrrolidin-3-yl)-8-oxo-8,9-dihydro-7H-purin-7-yl)-N-(4-methylpyridin-2-yl)benzamide To a solution of ((R)-4-(6-amino-8-oxo-9-(pyrrolidin-3-yl)-8,9-dihydro-7H-purin-7-yl)-N-(4-methylpyridin-2-yl)benzamide (1.0 eq) and 2-butynoic acid (1.2 eq) in DMF (20 mL/mmol) was added HATU (1.3 eq) followed by the addition of DIPEA (3.0 eq) at room temperature for about 10 min. The mixture was diluted with ethyl acetate and washed with water. The organic phase was separated, dried with sodium sulfate, and concentrated to dryness. The residue was purified by prep-HPLC chromatography (H$_2$O/MeCN+ 0.1% HCO$_2$H 95/5 to 0/100 gradient within 30 min) to give the title compound. LC-MS: 497 [M+H]$^-$. $^1$H NMR (300 MHz, CD$_3$OD) δ 8.19-8.09 (m, 5H), 7.58 (d, 2H), 7.01 (d, 1H), 5.29-5.14 (m, 1H), 4.36-4.29 (m, 0.5H), 4.15-4.06 (m, 1.5H), 3.92-3.78 (m, 1.5H), 3.57-3.53 (m, 0.5H), 2.87-2.78 (m, 1H), 2.42 (s, 3H), 2.40-2.36 (m, 1H), 2.02 (d, 3H).

Example 3—Synthesis of (R)-4-(6-amino-9-(1-but-2-ynoylpyrrolidin-3-yl)-8-oxo-8,9-dihydro-7H-purin-7-yl)-N-(5-(trifluoromethyl)pyridin-2-yl)benzamide

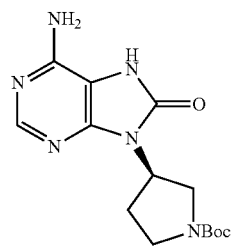

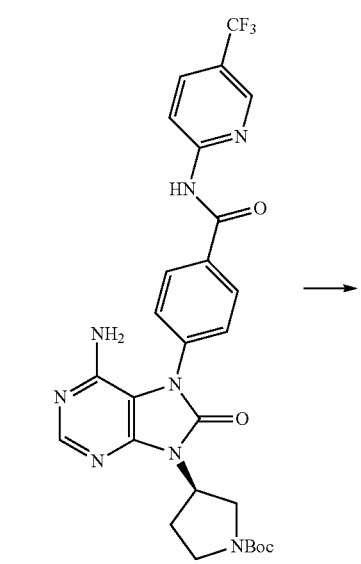

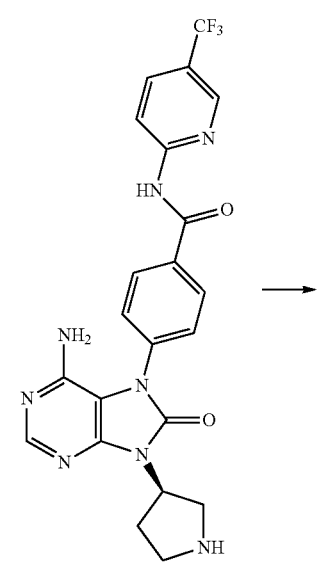

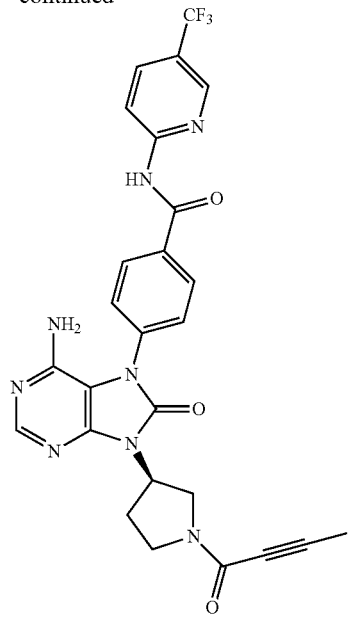

Step 1—Synthesis of (R)-tert-butyl 3-(6-amino-8-oxo-7-(4-(5-(trifluoromethyl)pyridin-2-ylcarbamoyl)phenyl)-7H-purin-9(8H)-yl)pyrrolidine-1-carboxylate To a suspension of (R)-tert-butyl 3-(6-amino-8-oxo-7H-purin-9(8H)-yl)pyrrolidine-1-carboxylate (1.0 eq) and 4-(5-(trifluoromethyl)pyridin-2-ylcarbamoyl)phenylboronic acid (2.0 eq) in dichloromethane (10 mL/mmol) was added copper(II) acetate (3.0 eq) and pyridine (6.0 eq). The mixture was stirred at about 35° C. overnight. The reaction mixture was filtered through a pad of Celite. The filtrate was diluted with ethyl acetate and washed with water. The organic phase was separated, dried with sodium sulfate, and concentrated to dryness. The residue was purified by flash column chromatography (silica, hexanes/ethyl acetate=1:1 to dichloromethane/methanol=10:1) followed by C18 chromatography (H$_2$O/MeCN+0.1% HCO$_2$H 95/5 to 0/100 gradient within 30 min) to give the title compound. LC-MS: 585 [M+H]$^+$

Step 2—Synthesis of (R)-4-(6-amino-8-oxo-9-(pyrrolidin-3-yl)-8,9-dihydro-7H-purin-7-yl)-N-(5-(trifluoromethyl)pyridin-2-yl)benzamide (R)-tert-Butyl 3-(6-amino-8-oxo-7-(4-(5-(trifluoromethyl)pyridin-2-ylcarbamoyl)phenyl)-7H-purin-9(8H)-yl)pyrrolidine-1-carboxylate was treated with HCl/dioxane (4.0 M, 28 mL/mmol) at room temperature for about 1 h. The reaction was concentrated to dryness. The residue was used for the next step without further purification. LC-MS: 485 [M+H]$^+$

Step 3—Synthesis of (R)-4-(6-amino-9-(1-but-2-ynoylpyrrolidin-3-yl)-8-oxo-8,9-dihydro-7H-purin-7-yl)-N-(5-(trifluoromethyl)pyridin-2-yl)benzamide To a solution of (R)-4-(6-amino-8-oxo-9-(pyrrolidin-3-yl)-8,9-dihydro-7H-purin-7-yl)-N-(5-(trifluoromethyl)pyridin-2-yl)benzamide (1.0 eq) and 2-butynoic acid (1.2 eq) in DMF (14 mL/mmol) was added HATU (1.2 eq) followed by the addition of DIPEA (3.0 eq) at room temperature for about 10 min. The mixture was diluted with ethyl acetate and washed with water. The organic phase was separated, dried with sodium sulfate, and concentrated to dryness. The residue was purified by C18 chromatography (H$_2$O/MeCN+ 0.1% HCO$_2$H 95/5 to 0/100 gradient within 30 min) to give the title compound. LC-MS: 551 [M+H]$^+$. $^1$H NMR (300 MHz, CD$_3$OD) δ 8.69 (s, 1H), 8.51-8.49 (m, 1H), 8.30 (s, 1H), 8.20-8.13 (m, 3H), 7.66-7.63 (m, 2H), 5.32-5.27 (m, 1H), 4.36-4.32 (m, 0.5H), 4.16-4.06 (m, 1.5H), 3.89-3.80 (m, 1.5H), 3.59-3.55 (m, 0.5H), 2.80-2.73 (m, 1H), 2.46-2.39 (m, 1H), 2.03 (d, 3H).

Example 4—Synthesis of (R)-4-(6-amino-9-(1-but-2-ynoylpyrrolidin-3-yl)-8-oxo-8,9-dihydro-7H-purin-7-yl)-N-(6-cyanopyridin-2-yl)benzamide

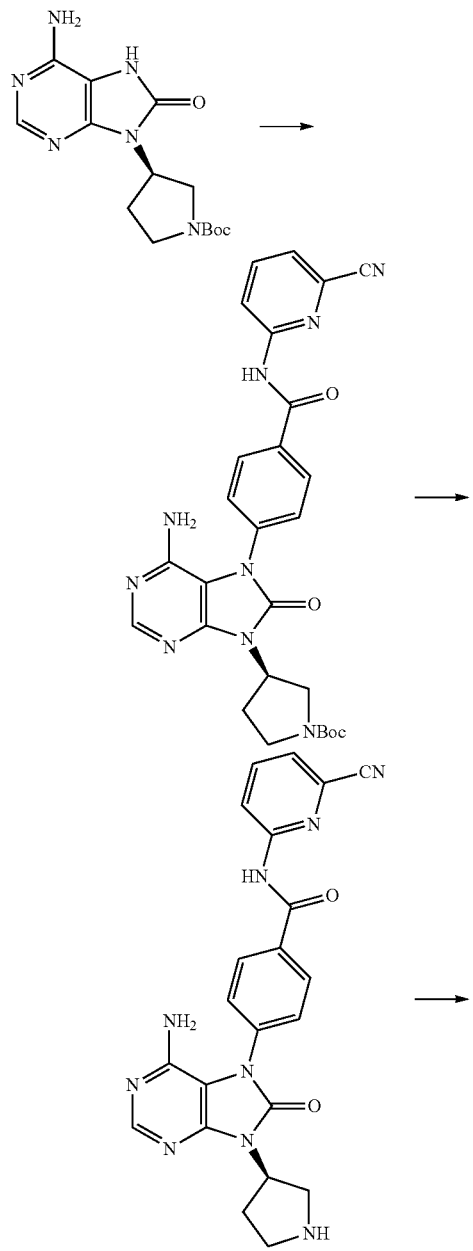

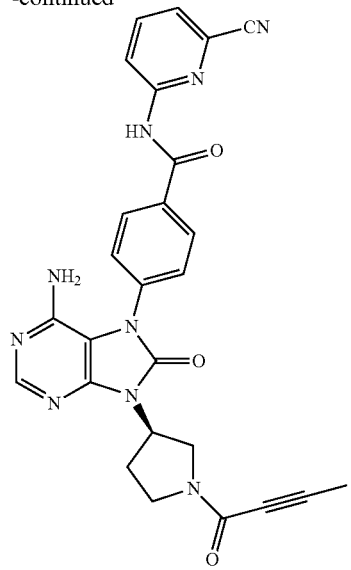

Step 1-Synthesis of (R)-tert-butyl 3-(6-amino-7-(4-(6-cyanopyridin-2-ylcarbamoyl)phenyl)-8-oxo-7H-purin-9(8H)-yl)pyrrolidine-1-carboxylate To a suspension of (R)-tert-butyl 3-(6-amino-8-oxo-7H-purin-9(8H)-yl)pyrrolidine-1-carboxylate (1.0 eq) and 4-(6-cyanopyridin-2-ylcarbamoyl)phenylboronic acid (2.0 eq) in dichloromethane (10 mL/mmol) was added copper(II) acetate (3.0 eq) and pyridine (6.0 eq). The mixture was stirred at about 35° C. overnight. The reaction mixture was filtered through a pad of Celite. The filtrate was diluted with ethyl acetate and washed with water. The organic phase was separated, dried with sodium sulfate, and concentrated to dryness. The residue was purified by flash column chromatography (silica, hexanes/ethyl acetate=1:1 to dichloromethane/methanol=10:1) followed by prep-HPLC C-18 chromatography (H$_2$O/MeCN+0.1% HCO$_2$H 95/5 to 0/100 gradient within 30 min) to give the title compound. LC-MS: 542 [M+H]$^+$ Step 2—Synthesis of (R)-4-(6-amino-8-oxo-9-(pyrrolidin-3-yl)-8,9-dihydro-7H-purin-7-yl)-N-(6-cyanopyridin-2-yl)benzamide To a solution of (R)-tert-butyl 3-(6-amino-7-(4-(6-cyanopyridin-2-ylcarbamoyl)phenyl)-8-oxo-7H-purin-9(8H)-yl) pyrrolidine-1-carboxylate in dichloromethane (12.5 ml/mmol) was treated with trifluoroacetic acid (12.5 ml/mmol) at room temperature for about 1 h. The reaction was concentrated to dryness. The residue was diluted with dichloromethane and washed with saturated sodium bicarbonate. The organic phase was separated, dried with sodium sulfate, and concentrated to dryness. The residue was used for the next step without further purification. LC-MS: 442 [M+H]$^+$ Step 3—Synthesis of (R)-4-(6-amino-9-(1-but-2-ynoylpyrrolidin-3-yl)-8-oxo-8,9-dihydro-7H-purin-7-yl)-N-(6-cyanopyridin-2-yl)benzamide To a solution of (R)-4-(6-amino-8-oxo-9-(pyrrolidin-3-yl)-8,9-dihydro-7H-purin-7-yl)-N-(6-cyanopyridin-2-yl)

benzamide (1.0 eq) and 2-butynoic acid (1.2 eq) in DMF (13.5 mL/mmol) was added HATU (1.2 eq) followed by the addition of DIPEA (3.0 eq) at room temperature for about 10 min. The mixture was diluted with ethyl acetate and washed with water. The organic phase was separated, dried with sodium sulfate, and concentrated to dryness. The residue was purified by C18 chromatography ($H_2O$/MeCN+0.1% $HCO_2H$ 95/5 to 0/100 gradient within 30 min) to give the title compound. LC-MS: 508 [M+H]$^+$. $^1$H NMR (300 MHz, $CD_3OD$) δ 8.60 (d, 1H), 8.29 (s, 1H), 8.17 (d, 2H), 8.01 (t, 1H), 7.62-7.57 (m, 3H), 5.32-5.27 (m, 1H), 4.36-4.30 (m, 0.5H), 4.16-4.03 (m, 1.5H), 3.92-3.80 (m, 1.5H), 3.59-3.55 (m, 0.5H), 2.86-2.72 (m, 1H), 2.46-2.37 (m, 1H), 2.03 (d, 3H).

Example 5—Synthesis of (R)-4-(6-amino-9-(1-but-2-ynoylpyrrolidin-3-yl)-8-oxo-8,9-dihydro-7H-purin-7-yl)-N-(thiazol-2-yl)benzamide

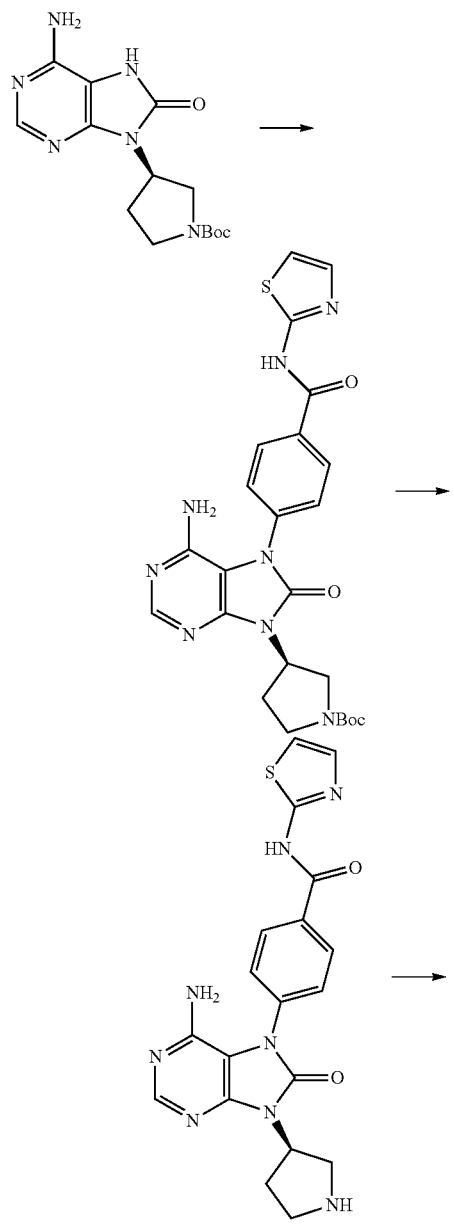

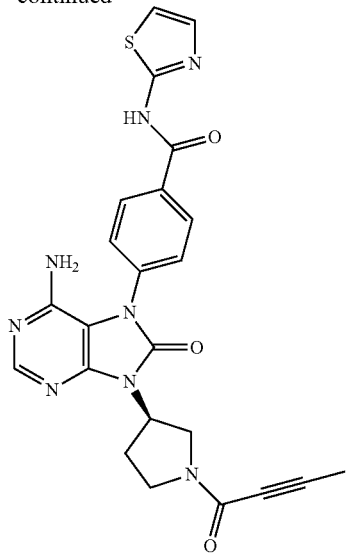

Step 1—Synthesis of (R)-tert-butyl 3-(6-amino-8-oxo-7-(4-(thiazol-2-ylcarbamoyl)phenyl)-7H-purin-9(8H)-yl)pyrrolidine-1-carboxylate To a suspension of (R)-tert-butyl 3-(6-amino-8-oxo-7H-purin-9(8H)-yl)pyrrolidine-1-carboxylate (1.0 eq) and 4-(thiazol-2-ylcarbamoyl)phenylboronic acid (1.5 eq) in dichloromethane (8 mL/mmol) was added copper(II) acetate (3.0 eq) followed by the addition of pyridine (6.0 eq). The mixture was stirred at about 35° C. overnight. The reaction mixture was filtered through a pad of Celite. The filtrate was diluted with ethyl acetate and washed with water. The organic phase was separated, dried with sodium sulfate, and concentrated to dryness. The residue was purified by flash column chromatography (silica, hexanes/ethyl acetate=1:1 to dichloromethane/methanol=10:1) followed by prep-HPLC C-18 chromatography ($H_2O$/MeCN+0.1% $HCO_2H$ 70/30 to 0/100 gradient within 30 min) to give the title compound. LC-MS: 523 [M+H]$^+$ Step 2—Synthesis of (R)-4-(6-amino-8-oxo-9-(pyrrolidin-3-yl)-8,9-dihydro-7H-purin-7-yl)-N-(thiazol-2-yl)benzamide (R)-tert-Butyl 3-(6-amino-8-oxo-7-(4-(thiazol-2-ylcarbamoyl)phenyl)-7H-purin-9(8H)-yl)pyrrolidine-1-carboxylate was treated with HCl/dioxane (4.0 M, 19 mL/mmol) at room temperature for about 1 h. The reaction was concentrated to dryness. The residue was purified by prep-HPLC C-18 chromatography ($H_2O$/MeCN+0.1% $HCO_2H$ 90/10 to 0/100 gradient within 30 min) to give the title compound. LC-MS: 423 [M+H]$^+$ Step 3—Synthesis of (R)-4-(6-amino-9-(1-but-2-ynoylpyrrolidin-3-yl)-8-oxo-8,9-dihydro-7H-purin-7-yl)-N-(thiazol-2-yl)benzamide To a solution of (R)-4-(6-amino-8-oxo-9-(pyrrolidin-3-yl)-8,9-dihydro-7H-purin-7-yl)-N-(thiazol-2-yl)benzamide (1.0 eq) and 2-butynoic acid (1.2 eq) in DMF (30 mL/mmol) was added HATU (1.3 eq) followed by the addition of DIPEA (3.0 eq) at room temperature for about 30 min. The mixture was diluted with ethyl acetate and washed with water. The organic phase was separated, dried with sodium sulfate, and concentrated to dryness. The residue was purified by C18 chromatography (H$_2$O/MeCN+0.1% TFA 95/5 to 0/100 gradient within 30 min) to give the title compound. LC-MS: 489 [M+H]$^+$. $^1$H NMR (300 MHz, CD$_3$OD) δ 8.29 (s, 1H), 8.21 (d, 2H), 7.64 (d, 2H), 7.54 (d, 1H), 7.21 (d, 1H), 5.31-5.26 (m, 1H), 4.36-4.30 (m, 0.5H), 4.16-4.03 (m, 1.5H), 3.92-3.80 (m, 1.5H), 3.59-3.55 (m, 0.5H), 2.86-2.72 (m, 1H), 2.46-2.37 (m, 1H), 2.03 (d, 3H).

Example 6—Synthesis of (R)-6-amino-9-(1-but-2-ynoylpyrrolidin-3-yl)-7-(6-phenoxypyridin-3-yl)-7H-purin-8(91/)-one

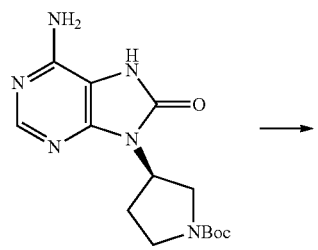

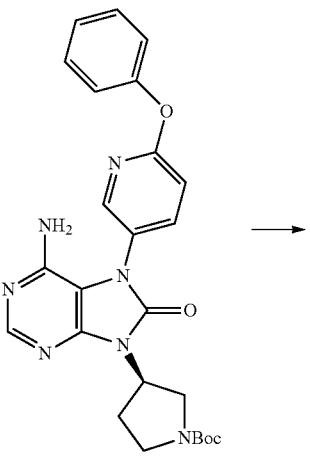

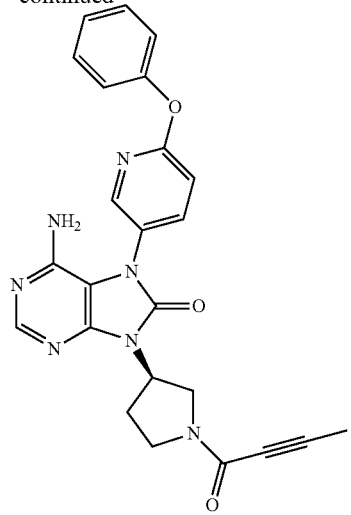

Step 1—Synthesis of (R)-tert-butyl 3-(6-amino-8-oxo-7-(6-phenoxypyridin-3-yl)-7H-purin-9(8H)-yl)pyrrolidine-1-carboxylate To a suspension of (R)-tert-butyl 3-(6-amino-8-oxo-7H-purin-9(8H)-yl)pyrrolidine-1-carboxylate (1.0 eq) and 6-phenoxypyridin-3-ylboronic acid (1.5 eq) in dichloromethane (10 mL/mmol) was added copper(II) acetate (3.0 eq) followed by the addition of pyridine (6.0 eq). The mixture was stirred at about 35° C. overnight. The reaction mixture was filtered through a pad of Celite. The filtrate was diluted with ethyl acetate and washed with water. The organic phase was separated, dried with sodium sulfate, and concentrated to dryness. The residue was purified by flash column chromatography (silica, hexanes/ethyl acetate=1:1 to dichloromethane/methanol=10:1) followed by C-18 chromatography (H$_2$O/MeCN+0.1% HCO$_2$H 95/5 to 0/100 gradient within 30 min) to give the title compound. LC-MS: 490 [M+H]$^+$ Step 2—Synthesis of (R)-6-amino-7-(6-phenoxypyridin-3-yl)-9-(pyrrolidin-3-yl)-7H-purin-8(91/)-one (R)-tert-Butyl 3-(6-amino-8-oxo-7-(6-phenoxypyridin-3-yl)-7H-purin-9 (8H)-yl)pyrrolidine-1-carboxylate was treated with HCl/dioxane (4.0 M, 19 mL/mmol) at room temperature for about 1 h. The reaction was concentrated to dryness. The residue was used for the next step without further purification. LC-MS: 390 [M+H]$^+$ Step 3—Synthesis of (R)-6-amino-9-(1-but-2-ynoylpyrrolidin-3-yl)-7-(6-phenoxypyridin-3-yl)-7H-purin-8(9H)-one To a solution of (R)-6-amino-7-(6-phenoxypyridin-3-yl)-9-(pyrrolidin-3-yl)-7H-purin-8(9H)-one (1.0 eq) and 2-butynoic acid (1.2 eq) in DMF (16 mL/mmol) was added HATU (1.3 eq) followed by the addition of DIPEA (3.0 eq) at room temperature for about 30 min. The mixture was diluted with ethyl acetate and washed with water. The organic phase was separated, dried with sodium sulfate, and concentrated to dryness. The residue was purified by C18 chromatography (H$_2$O/MeCN+0.1% HCO$_2$H 95/5 to 0/100 gradient within 30 min) to give the title compound. LC-MS: 456 [M+H]+. 1H NMR (300 MHz, CDCl3) δ 8.28-8.26 (m, 2H), 7.81-7.77 (m, 1H), 7.50-7.48 (m, 2H), 7.33-7.30 (m, 2H), 7.21-7.13 (m, 2H), 5.25-5.18 (m, 1H), 4.32-4.22 (m, 1.5H), 4.18-3.95 (m, 1.5H), 3.82-3.80 (m, 0.5H), 3.65-3.58 (m, 0.5H), 2.88-2.78 (m, 1H), 2.45-2.41 (m, 1H), 2.01 (d, 3H).

Example 7—Synthesis of N-(trans-4-(6-amino-8-oxo-7-(4-phenoxyphenyl)-7H-purin-9(8H)-yl)cyclohexyl)but-2-ynamide

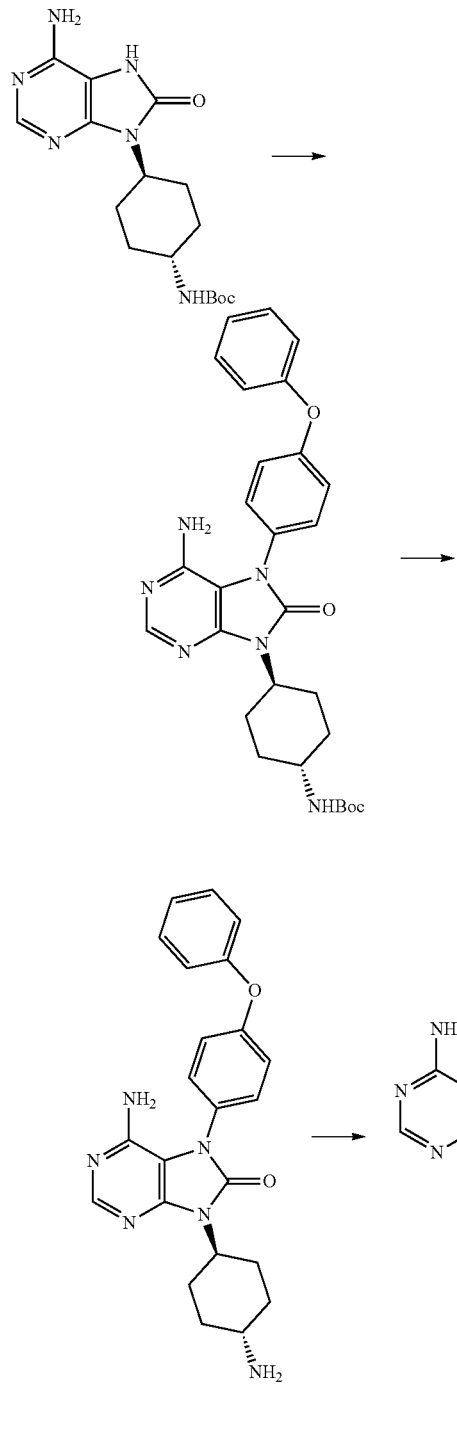

Step 1—Synthesis of tert-butyl trans-4-(6-amino-8-oxo-7-(4-phenoxyphenyl)-7H-purin-9(8H)-yl)cyclohexylcarbamate To a suspension of tert-butyl trans-4-(6-amino-8-oxo-7H-purin-9(8H)-yl)cyclohexylcarbamate (1.0 eq) and 4-phenoxyphenyl boronic acid (3.0 eq) in dichloromethane (25 mL/mmol) was added copper(II) acetate (3.0 eq) followed with pyridine (6.0 eq). The mixture was stirred at about 35° C. overnight. The reaction mixture was filtered through a pad of Celite to remove the solid, and washed with ethyl acetate. The filtrate was diluted with ethyl acetate and washed with water. The organic phase was separated, dried with sodium sulfate, and concentrated to dryness. The residue was purified by flash column chromatography (silica, hexanes/ethyl acetate=1:1 to dichloromethane/methanol=10:1) followed by C-18 chromatography (H2O/MeCN+ 0.1% HCO2H 95/5 to 0/100 gradient within 30 min) to give the title compound. LC-MS: 516 [M+H]+

Step 2—Synthesis of 6-amino-9-(trans-4-aminocyclohexyl)-7-(4-phenoxyphenyl)-7H-purin-8(9H)-one tert-Butyl trans-4-(6-amino-8-oxo-7-(4-phenoxyphenyl)-7H-purin-9(8H)-yl)cyclohexylcarbamate was treated with HCl/dioxane (4.0 M, 18 mL/mmol) at room temperature for about 1 h. The reaction was concentrated to dryness. The residue was used for the next step without further purification. LC-MS: 417 [M+H]+

Step 3—Synthesis of N-(trans-4-(6-amino-8-oxo-7-(4-phenoxyphenyl)-7H-purin-9(8H)-yl)cyclohexyl)but-2-ynamide To a solution of 6-amino-9-(trans-4-aminocyclohexyl)-7-(4-phenoxyphenyl)-7H-purin-8(9H)-one (1.0 eq) and 2-butynoic acid (1.2 eq) in DMF (15 mL/mmol) was added HATU (1.2 eq) followed by the addition of DIPEA (3.0 eq) at room temperature for 10 min. The mixture was diluted with ethyl acetate and washed with water. The organic phase was separated, dried with sodium sulfate, and concentrated to dryness. The residue was purified by C18 chromatography (H2O/MeCN+0.1% HCO2H 95/5 to 0/100 gradient within 30 min) to give the title compound. LC-MS: 483 [M+H]+. 1H NMR (300 MHz, CD3OD) δ 8.14 (s, 1H), 7.45-7.38 (m, 4H), 7.21-7.09 (m, 5H), 4.41-4.33 (m, 1H), 3.84-3.76 (m, 1H), 2.64-2.51 (m, 2H), 2.08-2.03 (m, 2H), 2.01 (s, 3H), 1.94-1.86 (m, 2H), 1.51-1.29 (m, 2H).

Example 8—Synthesis of N-(cis-4-(6-amino-8-oxo-7-(4-phenoxyphenyl)-7H-purin-9(8H)-yl)cyclohexyl)but-2-ynamide

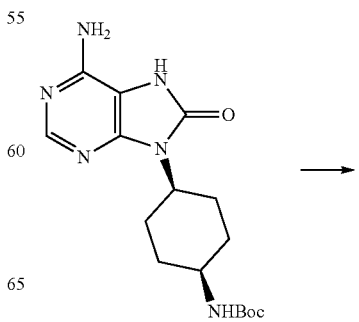

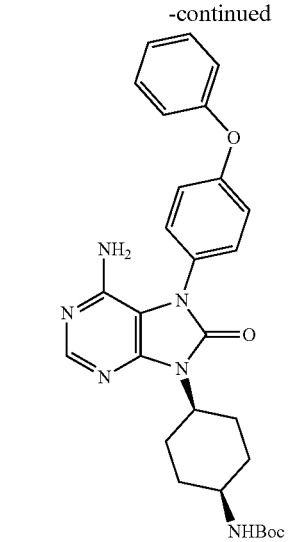

Step 1—Synthesis of tert-butyl cis-4-(6-amino-8-oxo-7-(4-phenoxyphenyl)-7H-purin-9(8H)-yl)cyclohexylcarbamate To a suspension of compound tert-butyl cis-4-(6-amino-8-oxo-7H-purin-9(8H)-yl)cyclohexylcarbamate (1.0 eq) and 4-phenoxyphenyl boronic acid (3.0 eq) in dichloromethane (17 mL/mmol) was added copper(II) acetate (3.0 eq) followed by the addition of pyridine (6.0 eq). The mixture was stirred at about 35° C. overnight. The reaction mixture was filtered through a pad of Celite. The filtrate was diluted with ethyl acetate and washed with water. The organic phase was separated, dried with sodium sulfate, and concentrated to dryness. The residue was purified by flash column chromatography (silica, hexanes/ethyl acetate=1:1 to dichloromethane/methanol=10:1) followed by C-18 chromatography (H$_2$O/MeCN+0.1% HCO$_2$H 95/5 to 0/100 gradient within 30 min) to give the title compound. LC-MS: 516 [M+H]$^+$

Step 2—Synthesis of 6-amino-9-(cis-4-aminocyclohexyl)-7-(4-phenoxyphenyl)-7H-purin-8 (9H)-one tert-Butyl cis-4-(6-amino-8-oxo-7-(4-phenoxyphenyl)-7H-purin-9 (8H)-yl)cyclohexylcarbamate was treated with HCl/dioxane (4.0 M, 7 mL/mmol) at room temperature for about 1 h. The reaction was concentrated to dryness. The residue was used for the next step without further purification. LC-MS: 416 [M+H]$^+$

Step 3—Synthesis of N-(cis-4-(6-amino-8-oxo-7-(4-phenoxyphenyl)-7H-purin-9(8H)-yl)cyclohexyl)but-2-ynamide To a solution of 6-amino-9-(cis-4-aminocyclohexyl)-7-(4-phenoxyphenyl)-7H-purin-8(9H)-one (1.0 eq) and 2-butynoic acid (1.2 eq) in DIVIF (7 mL/mmol) was added HATU (1.2 eq) followed by the addition of DIPEA (3.0 eq) at room temperature for about 30 min. The mixture was diluted with ethyl acetate and washed with water. The organic phase was separated, dried with sodium sulfate, and concentrated to dryness. The residue was purified by C18 chromatography (H$_2$O/MeCN+0.1% HCO$_2$H 95/5 to 0/100 gradient within 30 min) to give the title compound. $^1$H NMR (300 MHz, CD$_3$OD) δ 8.17 (s, 1H), 7.47-7.39 (m, 4H), 7.22-7.10 (m, 5H), 4.47-4.39 (m, 1H), 4.16-4.12 (m, 1H), 2.61-2.48 (m, 2H), 2.05-2.01 (m, 5H), 1.81-1.72 (m, 4H).

Example 9—Synthesis of 6-amino-9-(2-but-2-ynoyl-2-azaspiro[3.3]heptan-6-yl)-7-(4-phenoxyphenyl)-7H-purin-8(9H)-one

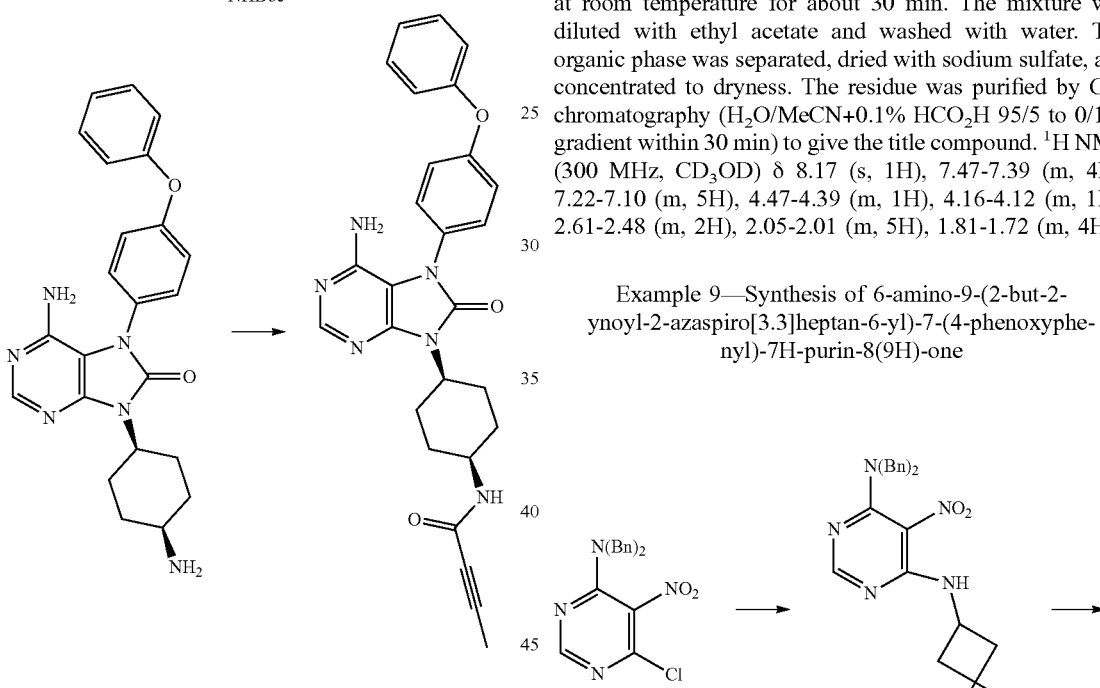

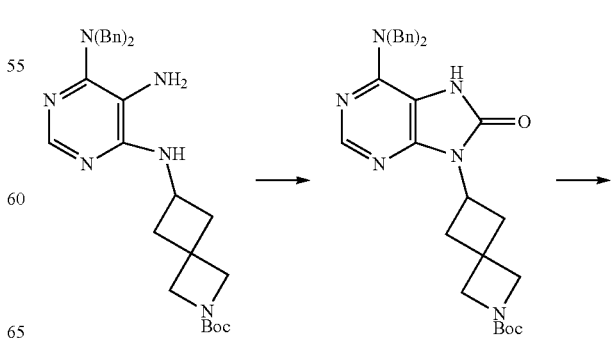

-continued

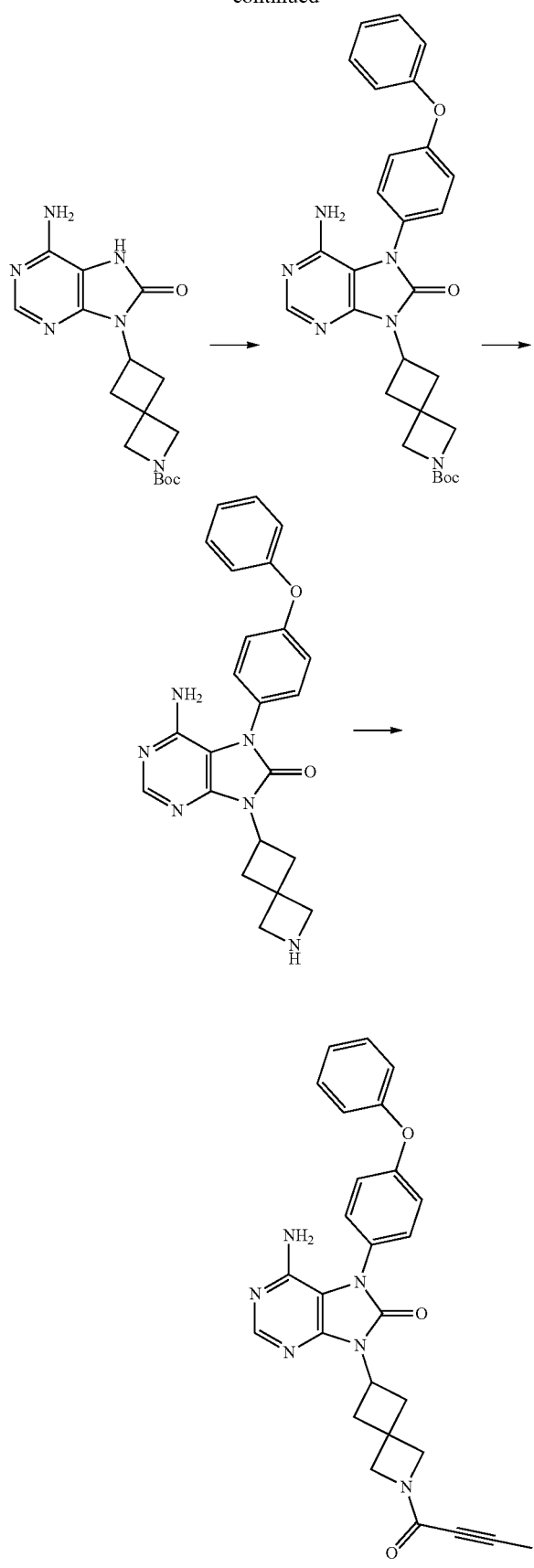

Step 1—Synthesis of tert-butyl 6-(6-(dibenzy-lamino)-5-nitropyrimidin-4-ylamino)-2-azaspiro[3.3]heptane-2-carboxylate A mixture of N,N-dibenzyl-6-chloro-5-nitropyrimidin-4-amine (1.0 eq), tert-butyl 6-amino-2-azaspiro[3.3]heptane-2-carboxylate (1.05 eq) and triethyl amine (1.2 eq) in dioxane (5 mL/mmol) was heated at about 50° C. for about 3 h. After being concentrated to remove dioxane, the resulting residue was purified by silica gel column, eluted with hexane/ethyl acetate (10/1 to 6/1) to give the title compound. LC-MS: 531 [M+1]$^+$ Step 2—Synthesis of tert-butyl 6-(5-amino-6-(dibenzylamino)pyrimidin-4-ylamino)-2-azaspiro[3.3]heptane-2-carboxylate To a suspension of zinc (10 eq) in ammonium chloride aqueous solution (6 eq) in ice-water bath was added dropwise a solution of tert-butyl 6-(6-(dibenzylamino)-5-nitropyrimidin-4-ylamino)-2-azaspiro[3.3]heptane-2-carboxylate (1.0 eq) in ethyl acetate (12 mL/mmol). The resulting suspension was allowed to stir at room temperature for about 2 h. The reaction mixture was filtered through a pad of Celite pad, and the filtrate was concentrated to dryness, which was used for the next step without further purification. LC-MS: 501 [M+1]$^+$ Step 3—Synthesis of tert-butyl 6-(6-(dibenzy-lamino)-8-oxo-7H-purin-9(8H)-yl)-2-azaspiro[3.3]heptane-2-carboxylate A mixture of tert-butyl 6-(5-amino-6-(dibenzylamino)pyrimidin-4-ylamino)-2-azaspiro[3.3]heptane-2-carboxylate (1.0 eq) and CDI (2.0 eq) in tetrahydrofuran (12.5 mL/mmol) was heated to about 60° C. for about 18 h. After being cooled to rt, and concentrated to remove THF, the residue was purified by silica gel column, eluted with dichloromethane/methanol (80:1 to 40:1) to give the title compound. LC-MS: 527 [M+1]$^+$ Step 4—Synthesis of tert-butyl 6-(6-amino-8-oxo-7H-purin-9(8H)-yl)-2-azaspiro[3.3]heptane-2-carboxylate To a solution of tert-butyl 6-(6-(dibenzylamino)-8-oxo-7H-purin-9(8H)-yl)-2-azaspiro[3.3]heptane-2-carboxylate in acetic acid (28 mL/mmol) was added palladium hydroxide (42 mg/mmol). The suspension under hydrogen balloon was heated at about 80° C. and hydrogenated using a balloon overnight. The mixture was filtered through a pad of Celite, and concentrated to give the title compound. LC-MS: 347 [M+1]$^-$ Step 5—Synthesis of tert-butyl 6-(6-amino-8-oxo-7-(4-phenoxyphenyl)-7H-purin-9(8H)-yl)-2-azaspiro[3.3]heptane-2-carboxylate To a suspension of tert-butyl 6-(6-amino-8-oxo-7H-purin-9(8H)-yl)-2-azaspiro[3.3]heptane-2-carboxylate (1.0 eq) and 4-phenoxyphenyl boronic acid (3.0 eq) in dichloromethane (17 mL/mmol) was added copper(II) acetate (3.0 eq) followed by the addition of pyridine (6.0 eq). The mixture was stirred at about 35° C. overnight. The reaction mixture was filtered through a pad of Celite. The filtrate was diluted with ethyl acetate and washed with water. The organic phase was separated, dried with sodium sulfate, and concentrated to dryness. The residue was purified by flash column chromatography (hexane/ethyl acetate from 3:1 to 2:1, then DCM/methanol from 100:1 to 50:1) to give the title compound. LC-MS: 515 [M+H]$^+$

Step 6—Synthesis of 6-amino-7-(4-phenoxyphenyl)-9-(2-azaspiro[3.3]heptan-6-yl)-7H-purin-8(9H)-one A solution of tert-butyl 6-(6-amino-8-oxo-7-(4-phenoxyphenyl)-7H-purin-9(8H)-yl)-2-azaspiro[3.3]heptane-2-carboxylate (1.0 eq) in DCM (11 mL/mmol) and TFA (20 eq) was allowed to stir at room temperature for about 5 hours. After concentration, the residue was purified by Biotage Isolera One, eluted with dichloromethane/methanol (from 50:1 to 10:1) to give the title compound.

Step 7—Synthesis of 6-amino-9-(2-but-2-ynoyl-2-azaspiro[3.3]heptan-6-yl)-7-(4-phenoxyphenyl)-7H-purin-8(9H)-one A solution of 2-butynoic acid (1.5 eq), HATU (1.3 eq), HOBt (1.3 eq), DIPEA (3 eq) in DCM (14 mL/mmol) was stirred at room temperature for about 20 minutes. To the reaction mixture was added a solution of 6-amino-7-(4-phenoxyphenyl)-9-(2-azaspiro[3.3]heptan-6-yl)-7H-purin-8(9H)-one (1.0 eq) in DCM (21 mL/mmol). The reaction mixture was stirred overnight. After concentration, the residue was diluted with dichloromethane (200 mL/mmol), washed with water (62 mL/mmol x 3). The DCM was dried and concentrated. The resulting residue was purified by prep-HPLC (A: water with 0.1% HCOOH; B: acetonitrile with 0.1% HCOOH; 0 to 100% B in 30 minutes) to give the title compound. LC-MS: 481 [M+H]$^-$

Example 10—Synthesis of 6-amino-9-(6-but-2-ynoyl-6-azaspiro[3.4]octan-2-yl)-7-(4-phenoxyphenyl)-7H-purin-8(9H)-one

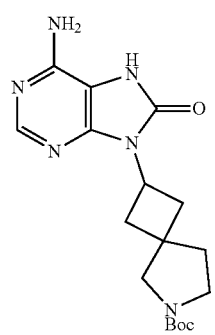

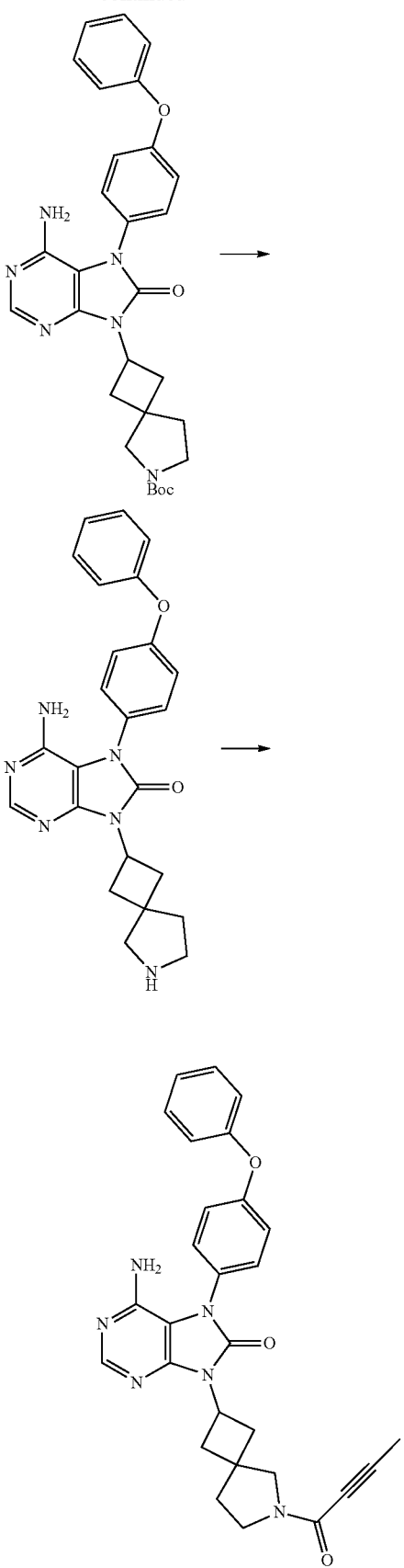

Step 1—Synthesis of tert-butyl 2-(6-amino-8-oxo-7-(4-phenoxyphenyl)-7H-purin-9(8H)-yl)-6-azaspiro[3.4]octane-6-carboxylate To a solution of tert-butyl 2-(6-amino-8-oxo-7H-purin-9(8H)-yl)-6-azaspiro[3.4]octane-6-carboxylate (1.0 eq) in DCM (15 mL/mmol) was added triethylamine (2.0 eq), copper(II) acetate (0.2 eq), and 4-phenoxyphenyl boronic acid (2.0 eq). The mixture was stirred at room temperature overnight. The reaction mixture was filtered through a Celite pad. The filtrate was concentrated to dryness. Purification using prep-TLC (DCM/methanol, 50:1) yielded the title compound. LC-MS: 529 [M+H]$^+$

Step 2—Synthesis of 6-amino-7-(4-phenoxyphenyl)-9-(6-azaspiro[3.4]octan-2-yl)-7H-purin-8(9H)-one To a solution of tert-butyl 2-(6-amino-8-oxo-7-(4-phenoxyphenyl)-7H-purin-9(8H)-yl)-6-azaspiro[3.4]octane-6-carboxylate(1.0 eq) in DCM (26 mL/mmol) was added TFA (20 eq). The solution was allowed to stir at room temperature for about 5 h. After concentration, the residue was purified by Biotage Isolera One, eluted with dichloromethane/methanol (from 50:1 to 10:1) to give the title compound. LC-MS: 429 [M+H]$^+$

Step 3—Synthesis of 6-amino-9-(6-but-2-ynoyl-6-azaspiro[3.4]octan-2-yl)-7-(4-phenoxyphenyl)-7H-purin-8(9H)-one A solution of 2-butynoic acid (1.5 eq), HATU (1.3 e.g.), DIPEA (5 eq) and 6-amino-7-(4-phenoxyphenyl)-9-(6-azaspi ro[3.4]octan-2-yl)-7H-purin-8(9H)-one in DMF (12.5 mL/mmol) was stirred at room temperature for about 2 hours. After concentration to remove DMF, the residue was diluted with dichloromethane (210 mL/mmol), washed with water (62 mL/mmol×3). The DCM was dried and concentrated. The resulting residue was purified by prep-HPLC (A: water with 0.1% HCOOH; B: acetonitrile with 0.1% HCOOH; 0 to 100% B in 30 minutes). The desired fractions were lyophilized to yield the title compound. LC-MS: 495 [M+H]$^+$

Example 11—Synthesis of N-(2-(6-amino-8-oxo-7-(4-phenoxyphenyl)-7H-purin-9(8H)-ypethyl)-N-methylbut-2-ynamide

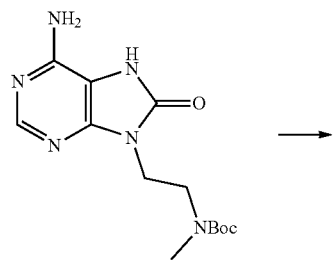

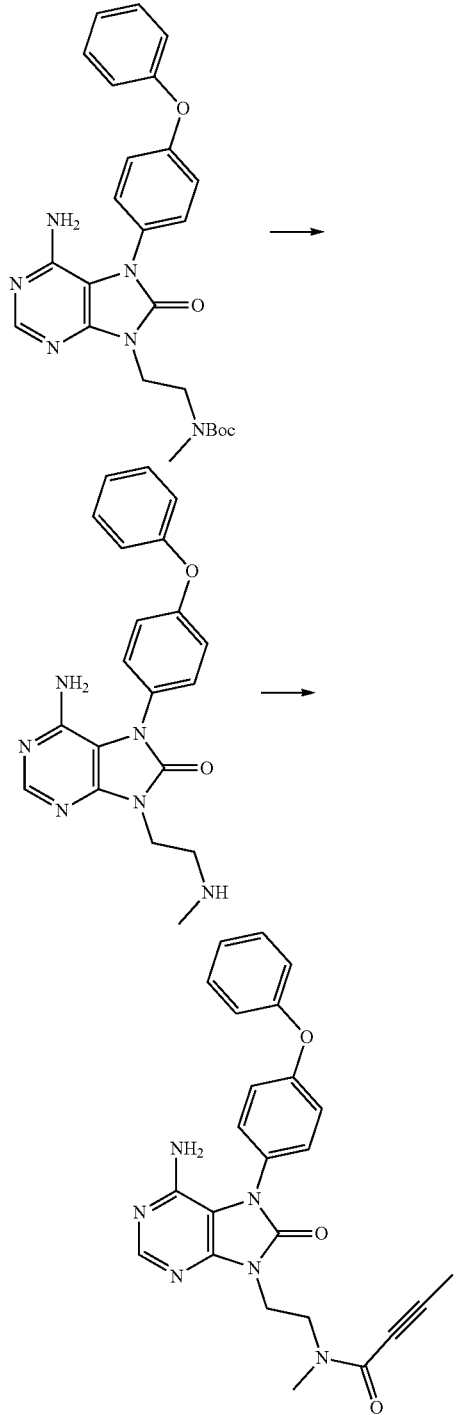

Step 1—Synthesis of tert-butyl 2-(6-amino-8-oxo-7-(4-phenoxyphenyl)-7H-purin-9(8H)-yl)ethyl(methyl)carbamate To a suspension of tert-butyl 2-(6-amino-8-oxo-7H-purin-9(8H)-yl)ethyl(methyl)carbamate (1.0 eq) and 4-phenoxyphenylboronic acid (1.5 eq) in dichloromethane (5 mL) was added copper(II) acetate (3.0 eq) followed by the addition of pyridine (6.0 eq). The mixture was stirred at about 35° C. overnight. The reaction mixture was filtered through a pad of Celite. The filtrate was diluted with ethyl acetate and washed with water. The organic phase was separated, dried with sodium sulfate, and concentrated to dryness. The residue was purified by flash column chromatography (silica, hexanes/ethyl acetate=1:1 to dichloromethane/methanol=10:1) to give the title compound. LC-MS: 477 [M+H]+

Step 2—Synthesis of 6-amino-9-(2-(methylamino) ethyl)-7-(4-phenoxyphenyl)-7H-purin-8(9H)-one tert-Butyl 2-(6-amino-8-oxo-7-(4-phenoxyphenyl)-7H-purin-9(8H)-yl)ethyl(methyl)carbamate was treated with HCl/dioxane (4.0 M, 10 mL/mmol) at room temperature for about 1 h. The reaction was concentrated to dryness to give the title compound. The crude residue was used for the next step without further purification. LC-MS: 377 [M+H]+

Step 3-Synthesis of N-(2-(6-amino-8-oxo-7-(4-phenoxyphenyl)-7H-purin-9(8H)-ypethyl)-N-methylbut-2-ynamide To a solution of 6-amino-9-(2-(methylamino)ethyl)-7-(4-phenoxyphenyl)-7H-purin-8(9H)-one (1.0 eq) and 2-butynoic acid (1.2 eq) in DMF (1 mL) was added HATU (1.2 eq) followed by the addition of DIPEA (3.0 eq) at room temperature for about 30 min. The mixture was diluted with ethyl acetate and washed with water. The organic phase was separated, dried with sodium sulfate, and concentrated to dryness. The residue was purified by C18 chromatography (H$_2$O/MeCN+0.1% trifluoroacetic acid 90/10 to 0/100 gradient within 30 min) to give the title compound. LC-MS: 443 [M+H]+. $^1$H NMR (300 MHz, CDCl$_3$) δ 8.23 (s, 1H), 7.46-7.35 (m, 4H), 7.25-7.08 (m, 5H), 4.27-4.21 (m, 2H), 4.04-4.00 (m, 1H), 3.84-3.80 (m, 1H), 3.27 (s, 1.5H), 3.08 (s, 1.5H), 1.96 (s, 1.5H), 1.72 (s, 1.5H).

Example 12—Synthesis of (R)—N-(4-(6-amino-9-(1-but-2-ynoylpyrrolidin-3-yl)-8-oxo-8,9-dihydro-7H-purin-7-yl)phenyl)-4-methylbenzamide (R)—N-(4-(6-amino-9-(1-but-2-ynoylpyrrolidin-3-yl)-8-oxo-8,9-dihydro-7H-purin-7-yl)phenyl)-4-methylbenzamide was prepared by an analogous procedure to Example 1, using (4-(4-methylbenzamide)phenyl)boronic acid instead of 4-benzamidephenylboronic acid.

Example 13—Synthesis of (R)-4-(6-amino-9-(1-but-2-ynoylpyrrolidin-3-yl)-8-oxo-8,9-dihydro-7H-purin-7-yl)-N-phenylbenzamide (R)-4-(6-amino-9-(1-but-2-ynoylpyrrolidin-3-yl)-8-oxo-8,9-dihydro-7H-purin-7-yl)-N-phenylbenzamide was prepared by an analogous procedure to Example 1, using (4-(phenylcarbamoyl)phenyl)boronic acid instead of 4-benzamidephenylboronic acid.

Example 14—Activity of Compounds of Formulae (I)-(III)

The activity assay of compounds of Formulae (I)-(III) in inhibiting Bruton's Tyrosine Kinase was conducted as follows. The test compound was dissolved in and diluted with dimethylsulfoxide (DMSO) and diluted with assay buffer to make the final test compound solution. Reference compounds for assay control were prepared similarly. Compounds were tested at a range of concentrations from 1 μM to 30 μM. Full-length human BTK [2-659(end) amino acids of accession number NP_000052.1] was expressed as N-terminal His-tagged protein (79 kDa) using a baculovirus expression system. His-tagged BTK was purified by using Ni-NTA affinity chromatography.

Off-chip Mobility Shift Assay (MSA): Five μL of 4× compound solution, 5 μL of 4× Substrate/ATP/Metal solution, and 10 μL of 2× kinase solution were prepared with assay buffer (20 mM HEPES, 0.01% Triton X-100, 2 mM DTT, pH 7.5) and mixed and incubated in a well of a polypropylene 384 well microplate for 1 hour at room temperature. Seventy μIL of Termination Buffer (QuickScout Screening Assist MSA; Carna Biosciences) was added to the well. Then the reaction mixture was applied to LabChip system (Perkin Elmer), and the product and substrate peptide peaks were separated and quantitated. The kinase reaction was evaluated by the product ratio calculated from peak heights of product(P) and substrate(S) peptides (P/(P+S)). Reaction conditions for BTK using MSA platform with 1000 nM of Srctide as substract, ATP 75 μM for assay (72 μM Km), and 5 mM Mg. Staurosporine was used as positive control.

The readout value of reaction control (complete reaction mixture) was set as a 0% inhibition, and the readout value of background (Enzyme(−)) was set as a 100% inhibition, then the percent inhibition of each test solution was calculated. IC$_{50}$ value was calculated from concentration vs. % Inhibition curves by fitting to a four parameter logistic curve. Table 2 provides activity data for compounds of Formulae (I)-(III).

TABLE 2

| Inhibition of Bruton's Tyrosine Kinase | |
| --- | --- |
| Compound of Formulae (I)-(III) | Inhibition of Bruton's Tyrosine Kinase (IC$_{50}$ (nm)) |
| (R)-N-(4-(6-amino-9-(1-but-2-ynoylpyrrolidin-3-yl)-8-oxo-8,9-dihydro-7H-purin-7-yl)phenyl)benzamide | >10 |
| (R)-4-(6-amino-9-(1-but-2-ynoylpyrrolidin-3-yl)-8-oxo-8,9-dihydro-7H-purin-7-yl)-N-(4-methylpyridin-2-yl)benzamide | >10 |
| (R)-4-(6-amino-9-(1-but-2-ynoylpyrrolidin-3-yl)-8-oxo-8,9-dihydro-7H-purin-7-yl)-N-(5-(trifluoromethyl)pyridin-2-yl)benzamide | >10 |
| (R)-4-(6-amino-9-(1-but-2-ynoylpyrrolidin-3-yl)-8-oxo-8,9-dihydro-7H-purin-7-yl)-N-(6-cyanopyridin-2-yl)benzamide | >10 |
| (R)-4-(6-amino-9-(1-but-2-ynoylpyrrolidin-3-yl)-8-oxo-8,9-dihydro-7H-purin-7-yl)-N-(thiazol-2-yl)benzamide | >10 |
| (R)-6-amino-9-(1-but-2-ynoylpyrrolidin-3-yl)-7-(6-phenoxypyridin-3-yl)-7H-purin-8(9H)-one | >10 |
| N-(trans-4-(6-amino-8-oxo-7-(4-phenoxyphenyl)-7H-purin-9(8H)-yl)cyclohexyl)but-2-ynamide | <10 |
| N-(cis-4-(6-amino-8-oxo-7-(4-phenoxyphenyl)-7H-purin-9(8H)-yl)cyclohexyl)but-2-ynamide | <10 |
| 6-amino-9-(2-but-2-ynoyl-2-azaspiro[3.3]heptan-6-yl)-7-(4-phenoxyphenyl)-7H-purin-8(9H)-one | <10 |
| 6-amino-9-(6-but-2-ynoyl-6-azaspiro[3.4]octan-2-yl)-7-(4-phenoxyphenyl)-7H-purin-8(9H)-one | <10 |
| N-(2-(6-amino-8-oxo-7-(4-phenoxyphenyl)-7H-purin-9(8H)-yl)ethyl)-N-methylbut-2-ynamide | >10 |
| (R)-N-(4-(6-amino-9-(1-but-2-ynoylpyrrolidin-3-yl)-8-oxo-8,9-dihydro-7H-purin-7-yl)phenyl)-4-methylbenzamide | >10 |
| (R)-4-(6-amino-9-(1-but-2-ynoylpyrrolidin-3-yl)-8-oxo-8,9-dihydro-7H-purin-7-yl)-N-phenylbenzamide | >10 |

What is claimed is:

1. A compound of Formula (I):

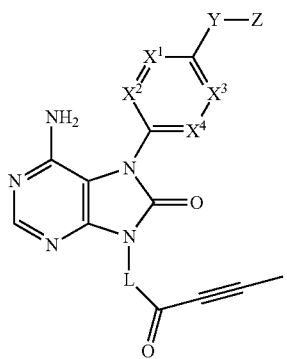

or a pharmaceutically acceptable salt, isomer, or mixture thereof, wherein:

$X^1$, $X^2$, $X^3$, and $X^4$ are each independently selected from CH or N, with the proviso that no more than two of $X^1$, $X^2$, $X^3$, and $X^4$ are N;

Y is selected from —O—, —NHC(O)—, —C(O)NH—, —NHS(O)$_2$—, and —S(O)$_2$NH—;

Z is selected from 6-membered aryl, 5-membered heteroaryl, and 6-membered heteroaryl; wherein the aryl or heteroaryl motif is optionally substituted with one, two, or three substituents selected from $C_1$-$C_8$ alkyl, $C_1$-$C_8$ alkoxy, CN, halogen, $C_1$-$C_8$ haloalkyl, NH$_2$, NH($C_1$-$C_8$ alkyl), and N($C_1$-$C_8$ alkyl)$_2$; and L is selected from —$C_3$-$C_6$ cycloalkyl-NH-, —$C_3$-$C_6$ cycloalkyl-N($C_1$-$C_8$ alkyl)-,

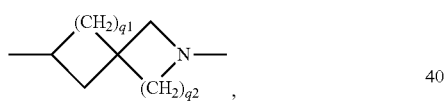

—(CH$_2$)$_{q3}$—(CH$_2$)$_{q3}$—N($C_1$-$C_8$ alkyl)-, and

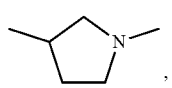

wherein q1, q2, and q3 are integers each independently selected from 1, 2, and 3;

with the proviso that if $X^1$, $X^2$, $X^3$, and $X^4$ are each CH and L is

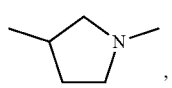

Y is not O.

2. The compound of claim 1, wherein $X^1$, $X^2$, $X^3$, and $X^4$ are each CH.

3. The compound of claim 1, wherein $X^1$ is N, and $X^2$, $X^3$, and $X^4$ are each independently CH.

4. The compound of claim 1, wherein Y is selected from —NHC(O)— and —C(O)NH-.

5. The compound of claim 1, wherein Z is phenyl, thiazolyl, or pyridinyl, wherein each of phenyl, thiazolyl, or pyridinyl is optionally substituted with methyl, ethyl, propyl, butyl, CN, or fluoromethyl, difluoromethyl, trifluoromethyl, fluoroethyl, difluoroethyl, trifluorethyl, fluoropropyl, difluoropropyl, or trifluoropropyl.

6. The compound of claim 1, wherein L is selected from —$C_3$-$C_6$ cycloalkyl-NH- and

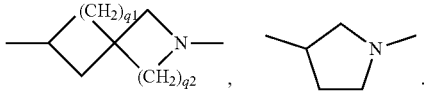

7. The compound of claim 6, where L is —$C_6$ cycloalkyl-NH-,

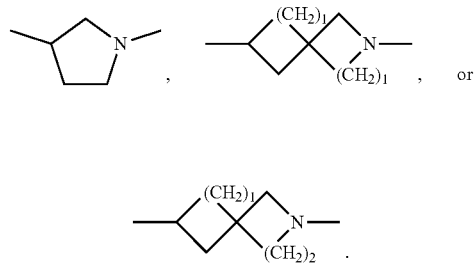

8. A compound of Formula (II):

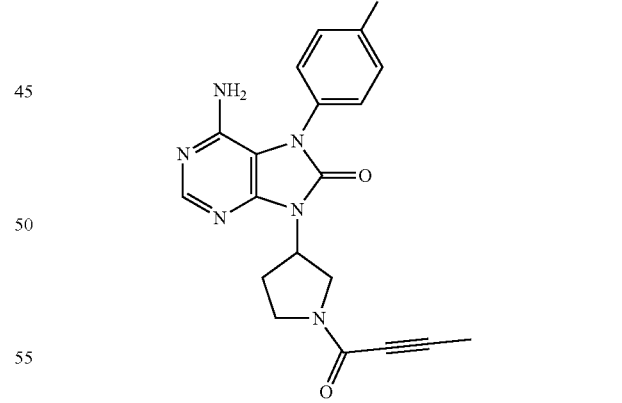

or a pharmaceutically acceptable salt, isomer, or mixture thereof;

wherein Y is —NHC(O)— or —C(O)NH—; and Z is 6-membered or 5-membered heteroaryl optionally substituted with one, two, or three substituents selected from $C_1$-$C_8$ alkyl, CN, and $C_1$-$C_8$ haloalkyl.

9. The compound of claim 8, wherein the compound has the structure of Formula (II-a):

(II-a)

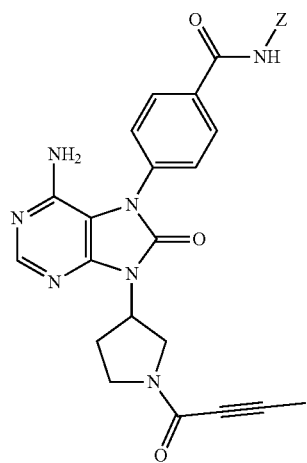

or a pharmaceutically acceptable salt, isomer, or mixture thereof;

wherein Z is 6-membered or 5-membered heteroaryl optionally substituted with one, two, or three substituents selected from $C_1$-$C_8$ alkyl, CN, and $C_1$-$C_8$ haloalkyl.

10. The compound of claim 8, wherein the compound has the structure of Formula (II-b):

(II-b)

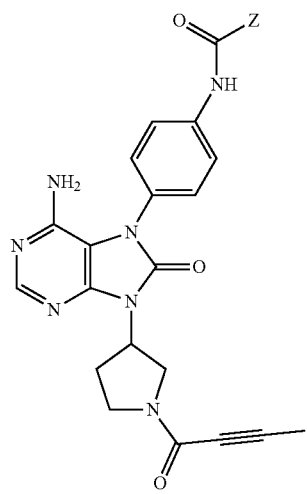

or a pharmaceutically acceptable salt, isomer, or mixture thereof;

wherein Z is 6-membered or 5-membered heteroaryl optionally substituted with one, two, or three substituents selected from $C_1$-$C_8$ alkyl, CN, and $C_1$-$C_8$ haloalkyl.

11. The compound of claim 8, wherein Z is thiazolyl or pyridinyl substituted with one, two, or three members selected from $C_1$-$C_8$ alkyl, CN, and $C_1$-$C_3$ haloalkyl.

12. A compound of Formula (III):

(III)

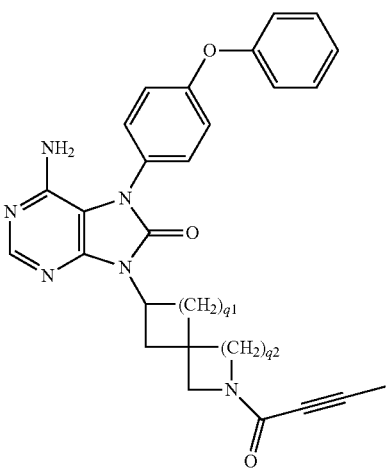

or a pharmaceutically acceptable salt, isomer, or mixture thereof;

wherein q1 is 1 and q2 is 1 or 2.

13. The compound of claim 1, wherein the compound is selected from:

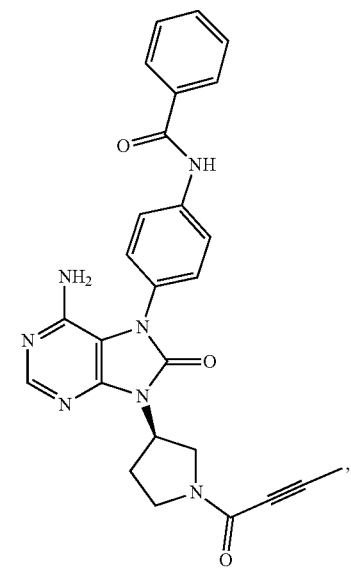

75
-continued
76
-continued
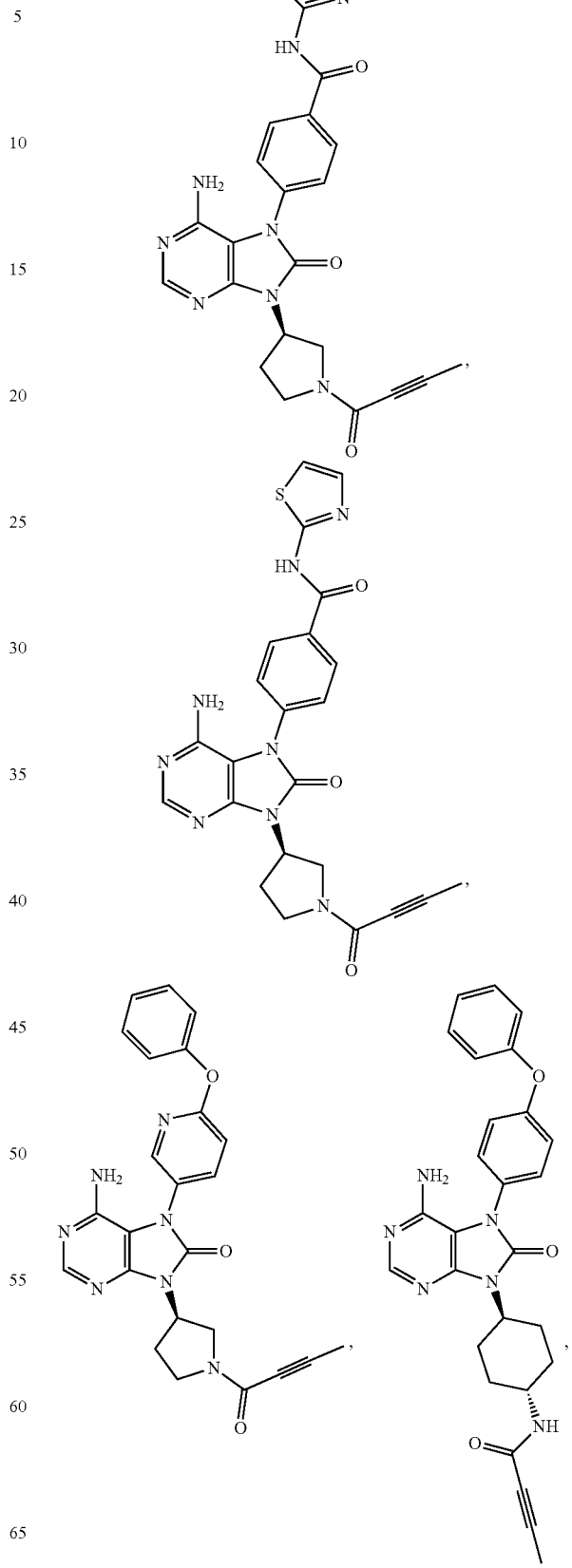

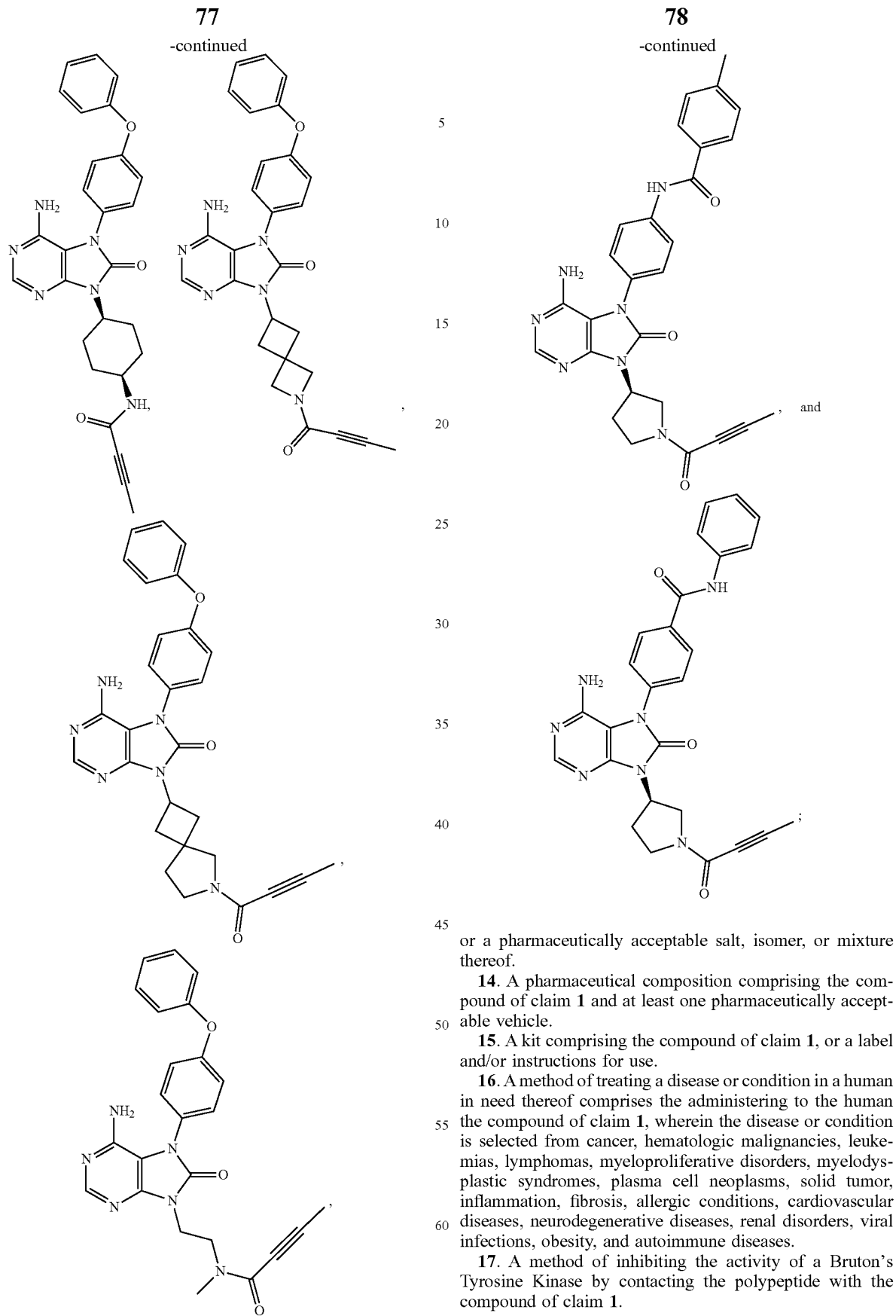

or a pharmaceutically acceptable salt, isomer, or mixture thereof.

14. A pharmaceutical composition comprising the compound of claim 1 and at least one pharmaceutically acceptable vehicle.

15. A kit comprising the compound of claim 1, or a label and/or instructions for use.

16. A method of treating a disease or condition in a human in need thereof comprises the administering to the human the compound of claim 1, wherein the disease or condition is selected from cancer, hematologic malignancies, leukemias, lymphomas, myeloproliferative disorders, myelodysplastic syndromes, plasma cell neoplasms, solid tumor, inflammation, fibrosis, allergic conditions, cardiovascular diseases, neurodegenerative diseases, renal disorders, viral infections, obesity, and autoimmune diseases.

17. A method of inhibiting the activity of a Bruton's Tyrosine Kinase by contacting the polypeptide with the compound of claim 1.

* * * * *

UNITED STATES PATENT AND TRADEMARK OFFICE
CERTIFICATE OF CORRECTION

PATENT NO. : 10,314,844 B2
APPLICATION NO. : 15/903295
DATED : June 11, 2019
INVENTOR(S) : Seung H. Lee et al.

Page 1 of 1

It is certified that error appears in the above-identified patent and that said Letters Patent is hereby corrected as shown below:

In the Claims

Column 71
Line 43, Claim 1: "-$(CH_2)_{q3}$-$(CH_2)_{q3}$-$N(C_1$-$C_8alkyl)$-," should read -- -$(CH_2)_{q3}$-NH-, -$(CH_2)_{q3}$-$N(C_1$-$C_8alkyl)$-, --

Signed and Sealed this
Eighteenth Day of February, 2020

Andrei Iancu
*Director of the United States Patent and Trademark Office*